(12) United States Patent
Yamazaki et al.

(10) Patent No.: US 10,894,117 B2
(45) Date of Patent: Jan. 19, 2021

(54) HOLLOW MOLDED ARTICLE

(71) Applicant: Kyoraku Co., Ltd., Kyoto (JP)

(72) Inventors: Daisuke Yamazaki, Yamato (JP);
Ryosuke Oki, Nagoya (JP); Tomohiro Taniguchi, Tokyo (JP)

(73) Assignee: Kyoraku Co., Ltd., Kyoto (JP)

( * ) Notice: Subject to any disclaimer, the term of this patent is extended or adjusted under 35 U.S.C. 154(b) by 0 days.

(21) Appl. No.: 15/302,327

(22) PCT Filed: Apr. 7, 2015

(86) PCT No.: PCT/JP2015/060895
§ 371 (c)(1),
(2) Date: Oct. 6, 2016

(87) PCT Pub. No.: WO2015/156299
PCT Pub. Date: Oct. 15, 2015

(65) Prior Publication Data
US 2017/0021077 A1   Jan. 26, 2017

(30) Foreign Application Priority Data

Apr. 7, 2014 (JP) .................................. 2014-078706
Jul. 22, 2014 (JP) .................................. 2014-149276
(Continued)

(51) Int. Cl.
*A61M 1/14* (2006.01)
*B29L 31/00* (2006.01)
(Continued)

(52) U.S. Cl.
CPC ............ *A61M 1/1629* (2014.02); *A61M 1/14* (2013.01); *A61M 1/36* (2013.01); *B29C 49/00* (2013.01);
(Continued)

(58) Field of Classification Search
CPC ......... B29C 51/10; B29C 51/30; B29C 51/02; B29C 51/00; B29C 49/48; B29C 49/04;
(Continued)

(56) References Cited

U.S. PATENT DOCUMENTS 4,617,161 A * 10/1986 Rollins .................. B01D 63/02
210/321.8
5,145,068 A * 9/1992 Schmitz .................. B29C 51/00
206/312

(Continued)

FOREIGN PATENT DOCUMENTS

DE    102010003642 A1    9/2011
EP         2116269 A1   11/2009
(Continued)

*Primary Examiner* — Nam X Nguyen
*Assistant Examiner* — Julia L. Wun
(74) *Attorney, Agent, or Firm* — Maier & Maier, PLLC

(57) ABSTRACT

Disclosed is a hollow molded article which has an opening portion communicating with a flow channel and which can be manufactured simply. The hollow molded article includes a panel and flow channels. The panel includes a first resin sheet and a second resin sheet partly welded with the first resin sheet. The flow channels are disposed between the first resin sheet and the second resin sheet, and include connection portions for external connection which are disposed on a peripheral edge of the panel. The connection portions are formed by the first resin sheet and the second resin sheet.

2 Claims, 28 Drawing Sheets

(30) Foreign Application Priority Data

Jul. 22, 2014 (JP) ................................. 2014-149278
Jul. 22, 2014 (JP) ................................. 2014-149280

(51) Int. Cl.

| | | |
|---|---|---|
| *A61M 1/16* | (2006.01) | |
| *B29C 51/00* | (2006.01) | |
| *B29C 51/02* | (2006.01) | |
| *B29C 51/10* | (2006.01) | |
| *B29C 51/30* | (2006.01) | |
| *B29C 49/02* | (2006.01) | |
| *B29C 49/48* | (2006.01) | |
| *B29C 49/04* | (2006.01) | |
| *B29C 49/00* | (2006.01) | |
| *B29C 49/42* | (2006.01) | |
| *A61M 1/36* | (2006.01) | |
| *B29C 49/20* | (2006.01) | |

(52) U.S. Cl.
CPC .............. *B29C 49/02* (2013.01); *B29C 49/04* (2013.01); *B29C 49/041* (2013.01); *B29C 49/4278* (2013.01); *B29C 49/48* (2013.01); *B29C 51/00* (2013.01); *B29C 51/02* (2013.01); *B29C 51/10* (2013.01); *B29C 51/30* (2013.01); *A61M 2205/12* (2013.01); *A61M 2206/10* (2013.01); *A61M 2206/14* (2013.01); *A61M 2207/00* (2013.01); *B29C 2049/0057* (2013.01); *B29C 2049/047* (2013.01); *B29C 2049/0008* (2013.01); *B29C 2049/2047* (2013.01); *B29L 2031/7148* (2013.01)

(58) Field of Classification Search
CPC ..... B29C 49/02; B29C 49/00; B29C 49/0047; B29C 2049/0057; B29C 2049/4869; B29C 2049/4879; A61M 1/14

USPC ............................. 210/321.6, 321.72, 321.71
See application file for complete search history.

(56) References Cited

U.S. PATENT DOCUMENTS

| | | | |
|---|---|---|---|
| 5,429,485 | A | 7/1995 | Dodge |
| 5,843,544 | A * | 12/1998 | Andersen .............. B01F 3/1214 |
| | | | 428/36.5 |
| 5,882,516 | A | 3/1999 | Gross et al. |
| 2006/0226086 | A1 | 10/2006 | Robinson et al. |
| 2007/0278155 | A1 | 12/2007 | Lo et al. |
| 2009/0101566 | A1 | 4/2009 | Crnkovich et al. |
| 2009/0250846 | A1 * | 10/2009 | Criel ...................... B29C 66/54 |
| | | | 264/511 |
| 2010/0087771 | A1 | 4/2010 | Karakama et al. |
| 2010/0129897 | A1 | 5/2010 | Murakami |
| 2010/0294398 | A1 | 11/2010 | Lauer et al. |
| 2013/0075314 | A1 | 3/2013 | Nikolic et al. |
| 2015/0021255 | A1 * | 1/2015 | Takahashi ........... A61M 1/3646 |
| | | | 210/232 |

FOREIGN PATENT DOCUMENTS

| | | |
|---|---|---|
| JP | H03-032679 A | 2/1991 |
| JP | H05161836 A | 6/1993 |
| JP | H060060781 U | 8/1994 |
| JP | H06327768 A | 11/1994 |
| JP | 2006130306 A | 5/2006 |
| JP | 3831048 B2 | 10/2006 |
| JP | 2007-75763 A | 3/2007 |
| JP | 2007097746 A | 4/2007 |
| JP | 2008535575 A | 9/2008 |
| JP | 2010502405 A | 1/2010 |
| JP | 2010538803 A | 12/2010 |
| JP | 2013049196 A | 3/2013 |
| JP | 2013521910 A | 6/2013 |
| WO | 2009/039357 A2 | 3/2009 |
| WO | 2010/121740 A1 | 10/2010 |

* cited by examiner

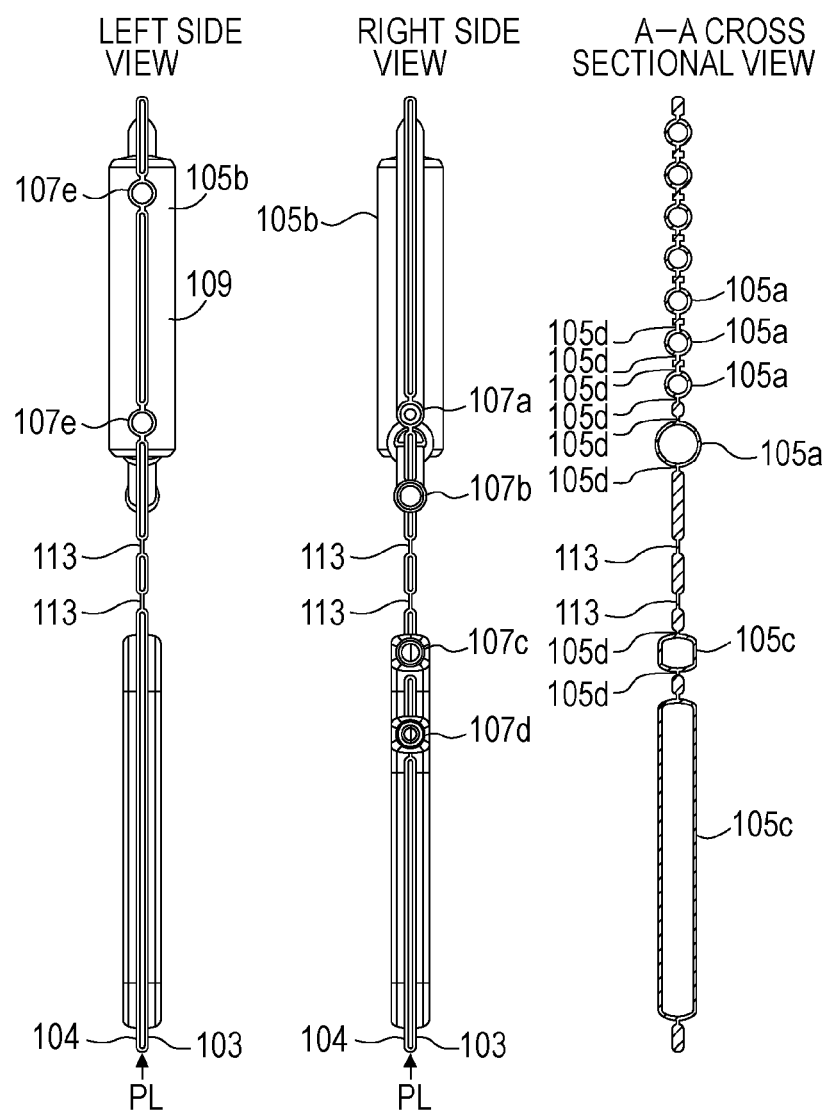

BOTTOM VIEW

F-F CROSS SECTIONAL VIEW

B-B ENLARGED CROSS SECTIONAL VIEW

C-C ENLARGED CROSS SECTIONAL VIEW

D-D ENLARGED CROSS SECTIONAL VIEW

E-E ENLARGED CROSS SECTIONAL VIEW ary process becomes all the hollow molded article manufacturing process becomes all the more complex.

HOLLOW MOLDED ARTICLE

CROSS-REFERENCE TO RELATED APPLICATIONS

This is a U.S. national phase application under 35 U.S.C. § 371 of International Patent Application No. PCT/JP2015/060895, filed on Apr. 7, 2015, and claims benefit of priority to Japanese Patent Application Nos. 2014-078706, filed Apr. 7, 2014, 2014-149276, filed Jul. 22, 2014, 2014-149278, filed Jul. 22, 2014, and 2014-149280, filed Jul. 22, 2014. The entire contents of these applications are hereby incorporated by reference.

TECHNICAL FIELD

The present invention relates to a hollow molded article.

BACKGROUND

Japanese Unexamined Patent Application Publication No. 2013-49196A (JP 2013-49196A) discloses a method for manufacturing a hollow molded article including a flow channel, by affixing two resin sheets which have grooves. The flow channel communicates with an opening portion provided in the side of the hollow molded article. Into the opening portion, the tip end of a water injection pipe or the like is inserted. Accordingly, the inner diameter of the opening portion is required to be highly accurately regulated so as to prevent liquid leakage at the connection portion. In JP 2013-49196A, when the hollow molded article is manufactured by vacuum molding, a core is placed between the two resin sheets at the position corresponding to the opening portion of the hollow molded article, so as to highly accurately regulate the inner diameter of the opening portion of the hollow molded article.

The method according to JP 2013-49196A enables highly accurate regulation of the inner diameter of the opening portion of the hollow molded article. However, a core must be disposed between the two resin sheets at the time of molding. Accordingly, the method has the problem that the hollow molded article manufacturing process becomes all the more complex.

A blood purification circuit panel as a hollow molded article, such as a blood purification circuit including a dialyzer, is disclosed in Patent Japanese Unexamined Patent Application Publication No. H05-161836A and Japanese Patent No. 3831048, for example.

A dialyzer contains a plurality (8,000 to 20,000) of thin pipes made of artificial membrane, and is configured to cause blood from a blood inlet pipe to be discharged out of a blood discharge pipe via the thin pipes. The dialyzer is also configured to cause a dialysate from a dialysate inlet pipe to flow outside the thin pipes and then be discharged out of a dialysate discharge pipe. In this way, substances are exchanged between the blood and the dialysate via the membrane of the thin pipes, whereby unwanted substances are moved to the dialysate while useful substances are moved into the blood.

Accordingly, the dialyzer is configured to have various necessary components attached to the periphery thereof via tubes, such as a pump for causing blood to flow into and out of the dialyzer, a pump for causing dialysate to flow into and out of the dialyzer, and a filter for filtering the dialysate.

However, each of the components is physically separated from the other components. Accordingly, each component must be connected using tubes, requiring very cumbersome work.

SUMMARY

The present invention has been made in view of the foregoing. The present invention provides a hollow molded article which has a connection portion communicating with a flow channel and which can be manufactured simply.

Another object of the present invention is to provide a blood purification circuit panel as follows. According to the panel, when the hollow molded article is a blood purification circuit panel, a panel including previously installed tubes and the like can be prepared. By easily and reliably attaching tubes and/or a dialyzer to the panel, a blood purification circuit can be configured.

The present invention is understood as follows.

(1) A hollow molded article includes: a panel including a first resin sheet and a second resin sheet partly welded with the first resin sheet; and a flow channel disposed between the first resin sheet and the second resin sheet, and including a connection portion for external connection disposed on a peripheral edge of the panel. The connection portion is formed by the first resin sheet and the second resin sheet.

(2) In the hollow molded article according to (1), the connection portion is a protruding pipe. The protruding pipe is disposed so as to communicate with the flow channel and protrude externally from the peripheral edge of the panel. The protruding pipe may include an opening portion at a tip end thereof.

(3) In the hollow molded article according to (2), the flow channel includes an agitation promoting portion. The agitation promoting portion may include a large diameter portion and a small diameter portion alternately disposed along a longitudinal direction. The small diameter portion may have a diameter smaller than a diameter of the large diameter portion.

(4) In the hollow molded article according to (1), the connection portion is a coupling portion. The coupling portion may be disposed so as to communicate with the flow channel and be recessed inward from the peripheral edge of the panel. The coupling portion may have a recessed pipe shape including an opening portion at a tip end thereof.

(5) In the hollow molded article according to (4), the coupling portion includes a first coupling portion disposed with one end thereof positioned at a part of the peripheral edge of the panel, and a second coupling portion disposed with one end thereof positioned at another portion of the peripheral edge of the panel. The hollow molded article may further include a first tube disposed between the first coupling portion and the second coupling portion and fitted with another end of the first coupling portion and with another end of the second coupling portion.

(6) In the hollow molded article according to (5), the coupling portion may have a smaller diameter at substantially a center than at both ends in an axial direction thereof.

(7) In the hollow molded article according to any one of (1) to (5), a dialyzer including a dialysate circulation pipe portion protruding from a side surface thereof is fixed to the panel. The panel includes an attachment section formed so as to protrude from a part of the peripheral edge and including a cut-out. The cut-out includes, on an opening side thereof, a narrowing portion decreasing a width of the cut-out. The hollow molded article may be configured such that the dialyzer is fixed to the panel with the circulation pipe portion fitted in the cut-out beyond the narrowing portion of the cut-out of the attachment section.

(8) In the hollow molded article according to (7), the circulation pipe portion of the dialyzer includes, around the pipe, a flange portion having an annular groove along a circumferential direction. The hollow molded article may be configured such that the dialyzer is fixed to the panel with an inner peripheral portion of the cut-out of the attachment section fitted in the annular groove of the flange portion.

(9) In the hollow molded article according to any one of (1) to (5), the hollow molded article further includes a tubular dialyzer and a securing band. The tubular dialyzer is disposed adjacent to one side of the panel, with a longitudinal direction of the tubular dialyzer disposed in parallel with the one side. The securing band may be fixed to the panel with one end of the securing band facing a first surface on the one side of the panel, and with the other end of the securing band passed around a peripheral surface of the dialyzer and locked on a second surface on the one side of the panel

(10) In the hollow molded article according to (9), the hollow molded article includes a plurality of the securing bands disposed along the longitudinal direction of the dialyzer. The first surface and the second surface may be different between the securing bands.

According to the present invention, a hollow molded article which includes a connection portion communicating with a flow channel and which can be simply manufactured can be obtained.

In addition, according to the present invention, when the hollow molded article is a blood purification circuit panel, a panel including previously installed tubes and the like can be prepared. Tubes and/or a dialyzer can be easily and reliably attached to the panel to configure a blood purification circuit. The present invention can provide a blood purification circuit panel including such blood purification circuit.

BRIEF DESCRIPTION OF THE DRAWINGS

FIG. 3(a) shows a left side view of the hollow molded article of FIG. 2, FIG. 3(b) shows a right side view of the hollow molded article of FIG. 2, and FIG. 3(c) shows an A-A cross sectional view of the hollow molded article of FIG. 2.

FIG. 5 illustrates a manufacturing process for the hollow molded article of FIG. 1.

FIG. 21 shows perspective views of a dialyzer and its vicinity.

DETAILED DESCRIPTION

First Example

In the following, a hollow molded article according to the first example of the present invention will be described. The hollow molded article according to the first example is not limited to any particular use, and may be applied for various uses involving circulation of liquid in the hollow molded article. Example uses are heat collectors and hot water panels. The configuration of flow channels in the hollow molded article and protruding pipes as connection portions for external connection, as will be described below, is an example, and their numbers, location, shape, and the like may be modified as needed.

Figure 1:
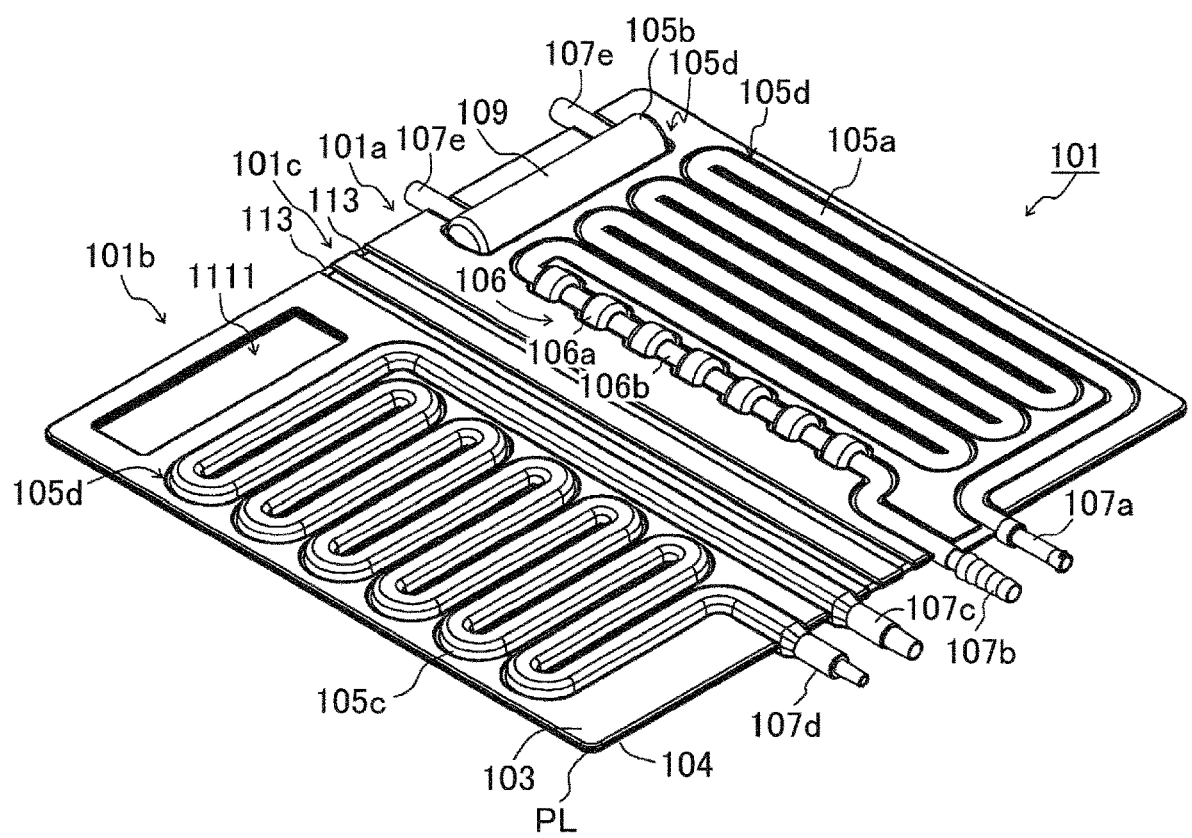
FIG. 1 is a perspective view illustrating a configuration of a hollow molded article according to the first example of the present invention.
Figure 2:
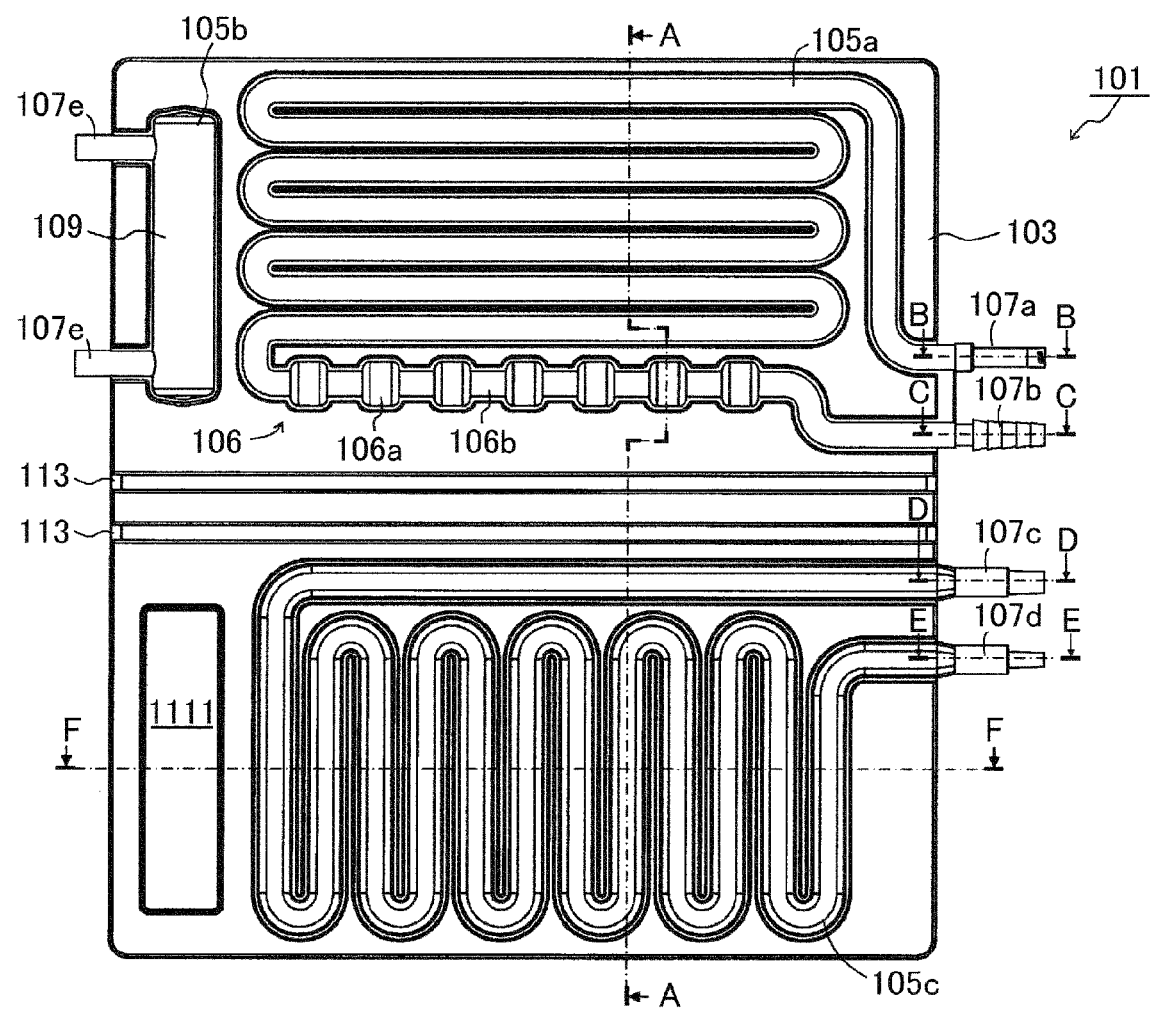
FIG. 2 is a plan view of the hollow molded article of FIG. 1.

As illustrated in FIG. 1, FIG. 2, and FIG. 3, a hollow molded article 101 according to the first example of the present invention includes a first resin sheet 103 and a second resin sheet 104 which are partly welded (the molded article including the welded first resin sheet 103 and second resin sheet 104 may be referred to as a panel). At the boundary of the resin sheets 103 and 104, there is formed a parting line PL which is, in the first example, disposed at substantially the center in the thickness direction of the hollow molded article 101. Between the resin sheets 103 and 104, flow channels 105a, 105b, and 105c through which liquid can be circulated are provided.

The hollow molded article 101 includes hinge portions 113 disposed at two locations which enable the hollow molded article 101 to be bent. The two hinge portions 113 are proximate and substantially parallel to each other. The hollow molded article 101 is divided into first and second sections 101a and 101b having the two hinge portions 113 disposed therebetween; and a third section 101c disposed between the two hinge portions 113. The flow channels 105a and 105b are provided in the first section 101a. The flow channel 105c is provided in the second section 101b. The hinge portions 113 have a thickness smaller than the thickness of portions other than the hinge portions 113. The hinge portions 113 can be formed, when molding the resin sheets 103 and 104 using molds 111 and 112 illustrated in FIG. 5, by making the distance between opposing protrusions of the molds 111 and 112 smaller in the hinge portions 113 than in other portions (preferably, smaller than the total thickness of the resin sheets 103 and 104 before molding). By folding the hollow molded article 101 at the hinge portions 113, the hollow molded article 101 can be made compact. In addition, by folding the hollow molded article 101 so as to sandwich an object to be heat-exchanged, such as a heater, heat-exchange efficiency can be increased.

The flow channel 105a communicates with protruding pipes 107a and 107b protruding from the peripheral edge of the hollow molded article 101. The protruding pipes 107a and 107b constitute connection portions for external connection. At the tip ends of the protruding pipes 107a and 107b, opening portions are provided. Accordingly, by coupling supply tubes (not illustrated) for supplying liquid into the flow channel 105a and discharge tubes (not illustrated) for discharging the liquid from the flow channel 105a with the protruding pipes 107a and 107b, the liquid can be circulated in the flow channel 105a. The supply tubes and discharge tubes can be coupled with the protruding pipes 107a and 107b by inserting the protruding pipes 107a and 107b into the openings of the supply tubes and discharge tubes. In order to couple the supply tubes and discharge tubes with the protruding pipes 107a and 107b accurately so as to prevent liquid leakage, the size accuracy of the outer diameter of the protruding pipes 107a and 107b must be high. In this respect, because the protruding pipes 107a and 107b are formed by molding the resin sheets 103 and 104 using the molds 111 and 112 illustrated in FIG. 5, the size accuracy of the outer diameter of the protruding pipes 107a and 107b can be increased without performing a special operation.

Figure 4A:
FIG. 4(a) is a bottom view of the hollow molded article of FIG. 2.
Figure 4B:
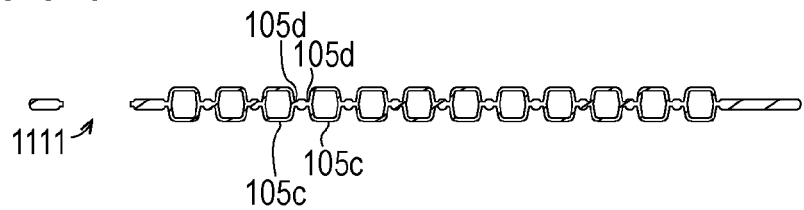
FIG. 4(b) is an F-F cross sectional view of the hollow molded article of FIG. 2.
Figure 4C:
FIG. 4(c) is a B-B enlarged cross sectional view of the hollow molded article of FIG. 2.
Figure 4D:
FIG. 4(d) is a C-C enlarged cross sectional view of the hollow molded article of FIG. 2.
Figure 4E:
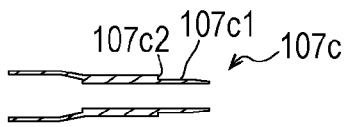
FIG. 4(e) is a D-D enlarged cross sectional view of the hollow molded article of FIG. 2.
Figure 4F:
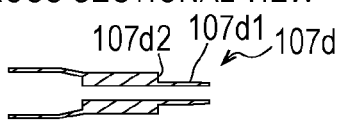
FIG. 4(f) is an E-E enlarged cross sectional view of the hollow molded article of FIG. 2.

The shape of the protruding pipes 107a and 107b is not particularly limited. The protruding pipes may have any shape which allows for coupling with the supply tubes and discharge tubes. For example, as illustrated in FIG. 4(c), the protruding pipe 107a includes a cylinder portion 107a1 with a protrusion 107a2 disposed on the outer surface at substantially the tip end thereof. The protrusion 107a2 resists the fall of the tube from the protruding pipe 107a. Further, as illustrated in FIG. 4(d), the protruding pipe 107b includes a cylinder portion 107b1 with a stepped protrusion 107b2 disposed on the outer surface at substantially the tip end thereof. The steps in the stepped protrusion 107b2 become higher with increasing distance from the tip end of the protruding pipe 107b. In this configuration, the outer diameter of the protruding pipe 107b becomes greater with increasing distance from the tip end of the protruding pipe 107b. Accordingly, even if the inner diameter of the tube into which the protruding pipe 107b is inserted is changed, the protruding pipe 107b can be reliably attached to the tube.

The flow channel 105a meanders in the first section 101a. At least a part of the flow channel 105a includes an agitation promoting portion 106 which promotes agitation of the liquid flowing in the flow channel 105a. The agitation promoting portion 106 includes large diameter portions 106a and small diameter portions 106b which are alternately disposed along the longitudinal direction, the small diameter portions having a smaller diameter than the large diameter portions 106a. In this configuration, the flow velocity of the liquid that flows through the agitation promoting portion 106 is varied, thereby promoting agitation of the liquid. In addition, along the side edges of the flow channel 105a, reduced-thickness welded portions 105d are provided. The reduced-thickness welded portions 105d can be formed by, when molding the resin sheets 103 and 104 using the molds 111 and 112, as illustrated in FIG. 5, making the distance between opposing protrusions of the molds 111 and 112 smaller than the total thickness of the resin sheets 103 and 104 prior to molding. The configuration enables the resin sheets 103 and 104 to be reliably welded, whereby liquid leakage from the flow channel 105a can be prevented.

Figure 5A:
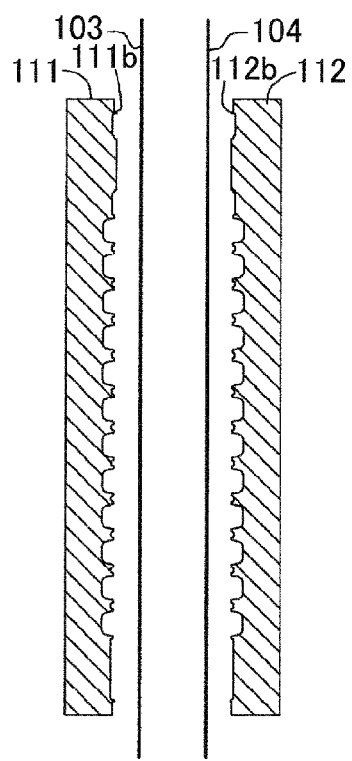
FIG. 5(a) illustrates a state prior to placing a resin sheet in intimate contact with a mold.

The flow channel 105b communicates with a pair of protruding pipes 107e protruding from the peripheral edge of the hollow molded article 101. The tip ends of the protruding pipes 107e include opening portions. The protruding pipes 107e can be coupled with a supply tube and a discharge tube, similarly to the protruding pipes 107a and 107b. The flow channel 105b includes a functional component accommodating portion 109. The functional component accommodating portion 109 can accommodate a functional component, such as a filter or a static mixer. A filter can be used to remove foreign substances in the liquid flowing in the flow channel 105b. A static mixer can be used to agitate the liquid flowing in the flow channel 105b. The functional component can be incorporated in the hollow molded article 101 by being placed in a portion between the resin sheets 103 and 104 corresponding to the functional component accommodating portion 109, before the molds 111 and 112 are closed, as illustrated in FIG. 5(c). The functional component accommodating portion 109 has a certain height. Accordingly, the second section 101b includes an opening portion 1111 at a location opposing the functional component accommodating portion 109 so that the functional component accommodating portion 109 will not interfere with the second section 101b when the hollow molded article 101 is folded at the hinge portions 113. In addition, as in the case of the flow channel 105a, reduced-thickness welded portions 105d are provided along the side edges of the flow channel 105b.

The flow channel 105c communicates with protruding pipes 107c and 107d protruding from the peripheral edge of the hollow molded article 101. The tip ends of the protruding pipes 107c and 107d include opening portions. Similarly to the protruding pipes 107a and 107b, the protruding pipes 107c and 107d can be coupled with a supply tube and a discharge tube. The protruding pipes 107c and 107d, as illustrated in FIGS. 4 (e) and (f), include substantially cylindrical insertion portions 107c1 and 107d1, and abutment portions 107c2 and 107d2. The abutment portions 107c2 and 107d2 abut on the tip ends of the tubes into which the insertion portions 107c1 and 107d1 are inserted. According to this configuration, by inserting the insertion portions 107c1 and 107d1 into the tubes until the abutment portions 107c2 and 107d2 abut on the tip ends of the tubes, the amount of insertion of the protruding pipes 107c and 107d into the tubes can be accurately defined. The flow channel 105c meanders in the second section 101b. Similarly to the flow channel 105a, reduced-thickness welded portions 105d are provided along the side edges of the flow channel 105c.

A method for manufacturing the hollow molded article 101 according to the first example will be described. First, as illustrated in FIG. 5(a), a pair of divided molds 111 and 112 with inner surface shapes corresponding to the shape of the hollow molded article 101 is prepared. Resin sheets (parisons) 103 and 104 in molten state are disposed between the molds 111 and 112. The details of the method for manufacturing the hollow molded article 101 will be described later.

Figure 5B:
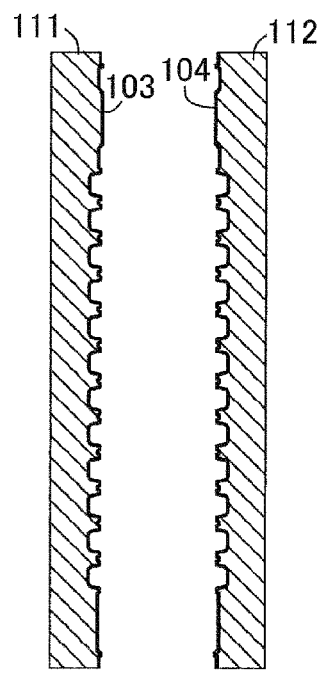
FIG. 5(b) illustrates a state after the resin sheet is placed in intimate contact with the mold.
Figure 5C:
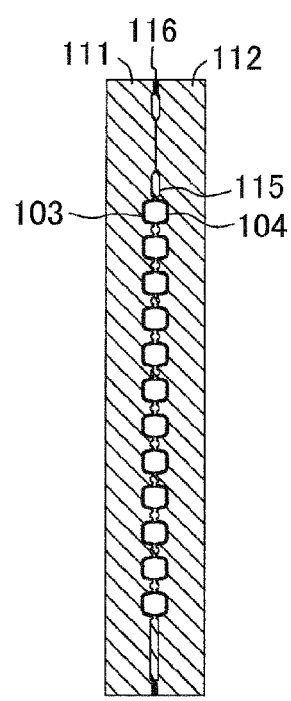
FIG. 5(c) illustrates a state after clamping of the mold.

Then, as illustrated in FIG. 5(b), the resin sheets 103 and 104 in molten state are suctioned from the side of the molds 111 and 112. As a result, the resin sheets 103 and 104 are placed in intimate contact with the molds 111 and 112.

The molds 111 and 112 are then clamped, as illustrated in FIG. 5(c), whereby the resin sheets 103 and 104 are partly welded. For example, the resin sheets 103 and 104 are welded at the peripheral edge portion of the hollow molded article 101, the peripheral edge portion of the opening portion 1111, the reduced-thickness welded portions 105d along the side edges of the flow channels 105a to 105c, and the hinge portions 113. In other portions, the resin sheets 103 and 104 may be welded, or the resin sheets 103 and 104 may have a gap therebetween. The molds 111 and 112 include pinch-off parts 111b and 112b surrounding a cavity 115 formed inside the molds 111 and 112. The resin sheets 103 and 104 are pinched by the pinch-off parts 111b and 112b and thereby crushed. Of the resin sheets 103 and 104, portions outside the cavity 115 correspond to a burr 116. The portions pinched by the pinch-off parts 111b and 112b define a cutoff line for the burr 116. In the first example, the protruding pipes 107a to 107e are provided protruding from the sides of the hollow molded article 101. The burr 116 is also formed over the boundary of the resin sheets 103 and 104 at the protruding pipes 107a to 107e. The burr 116 is also formed where the opening portion 1111 is provided.

The molds 111 and 112 are thereafter opened, the molded article is extracted, the burr 116 is removed, and the hollow molded article 101 illustrated in FIG. 1 is obtained.

(Invention According to Other Aspects)

The present invention may be understood as follows. The above description of the first example may be applied to the following aspects of the invention. According to the following aspects of the invention, the connection portions are not necessarily required to be protruding pipes.

According to another aspect of the present invention, a hollow molded article including a first resin sheet and a second resin sheet which are partly welded is provided. Between the first resin sheet and the second resin sheet, a flow channel is provided. The flow channel includes an agitation promoting portion. The agitation promoting portion includes a large diameter portion and a small diameter portion which are alternately disposed along the longitudinal direction, the small diameter portion having a smaller diameter than the large diameter portion. In this case, agitation of a liquid that flows in the flow channels can be promoted.

According to yet another aspect of the present invention, a hollow molded article including a first resin sheet and a second resin sheet which are partly welded is provided. Between the first resin sheet and the second resin sheet, a flow channel is provided. The hollow molded article includes a hinge portion enabling the hollow molded article to be bent. In this case, by folding the hollow molded article at the hinge portion, the hollow molded article can be made compact. In addition, by folding the hollow molded article so as to sandwich an object to be heat-exchanged, such as a heater, heat-exchange efficiency can be increased.

According to still another aspect of the present invention, a hollow molded article having a first resin sheet and a second resin sheet which are partly welded is provided. Between the first resin sheet and the second resin sheet, a flow channel is provided. The flow channel is provided with a functional component accommodating portion able to accommodate a functional component. In this case, the functional component, such as a filter or static mixer, can be accommodated in a functional component accommodating portion.

Second and Third Examples

Figure 6:
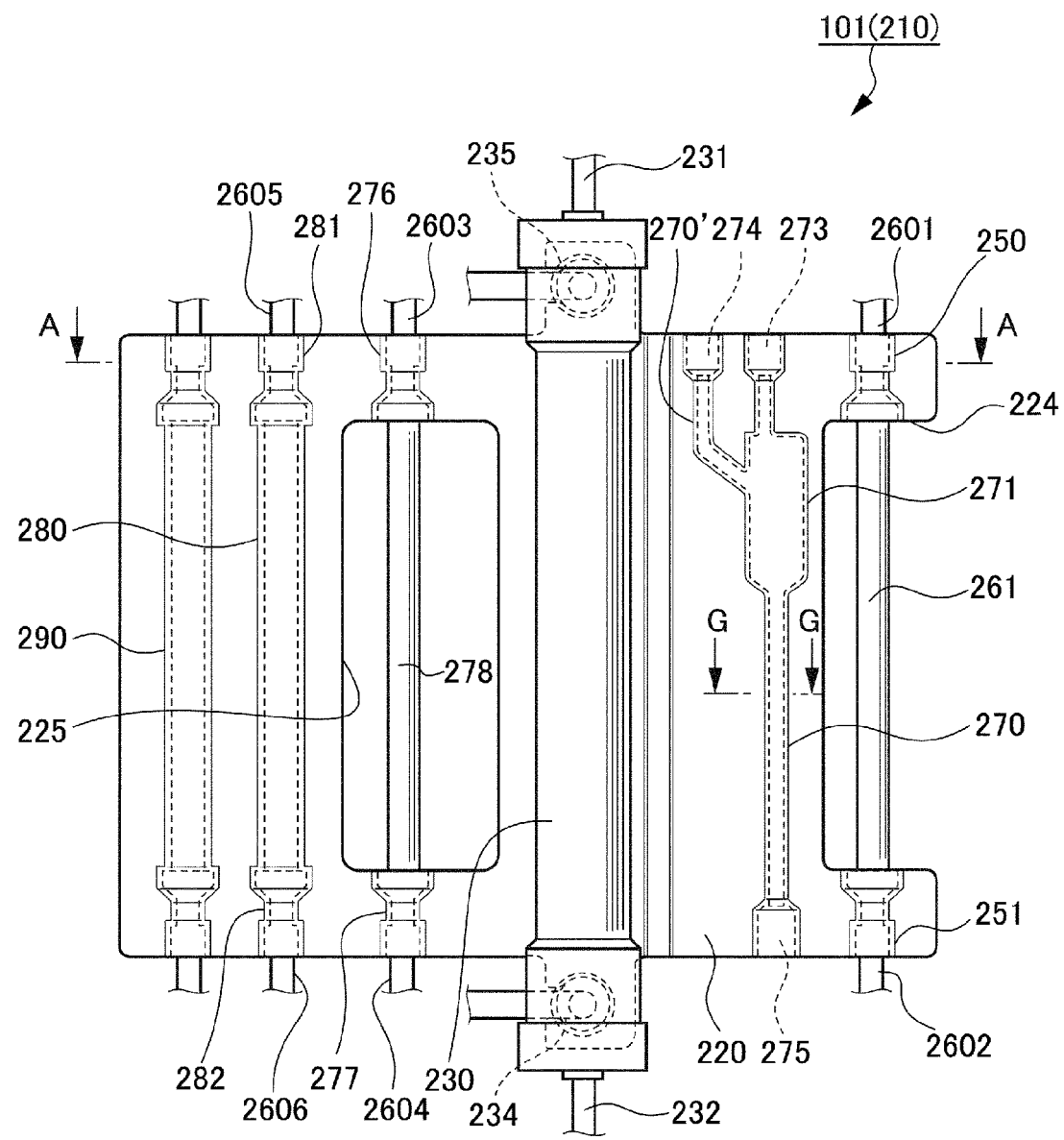
FIG. 6 is a front view illustrating the second and third examples of a hollow molded article (blood purification circuit panel) according to the present invention.
Figure 7:
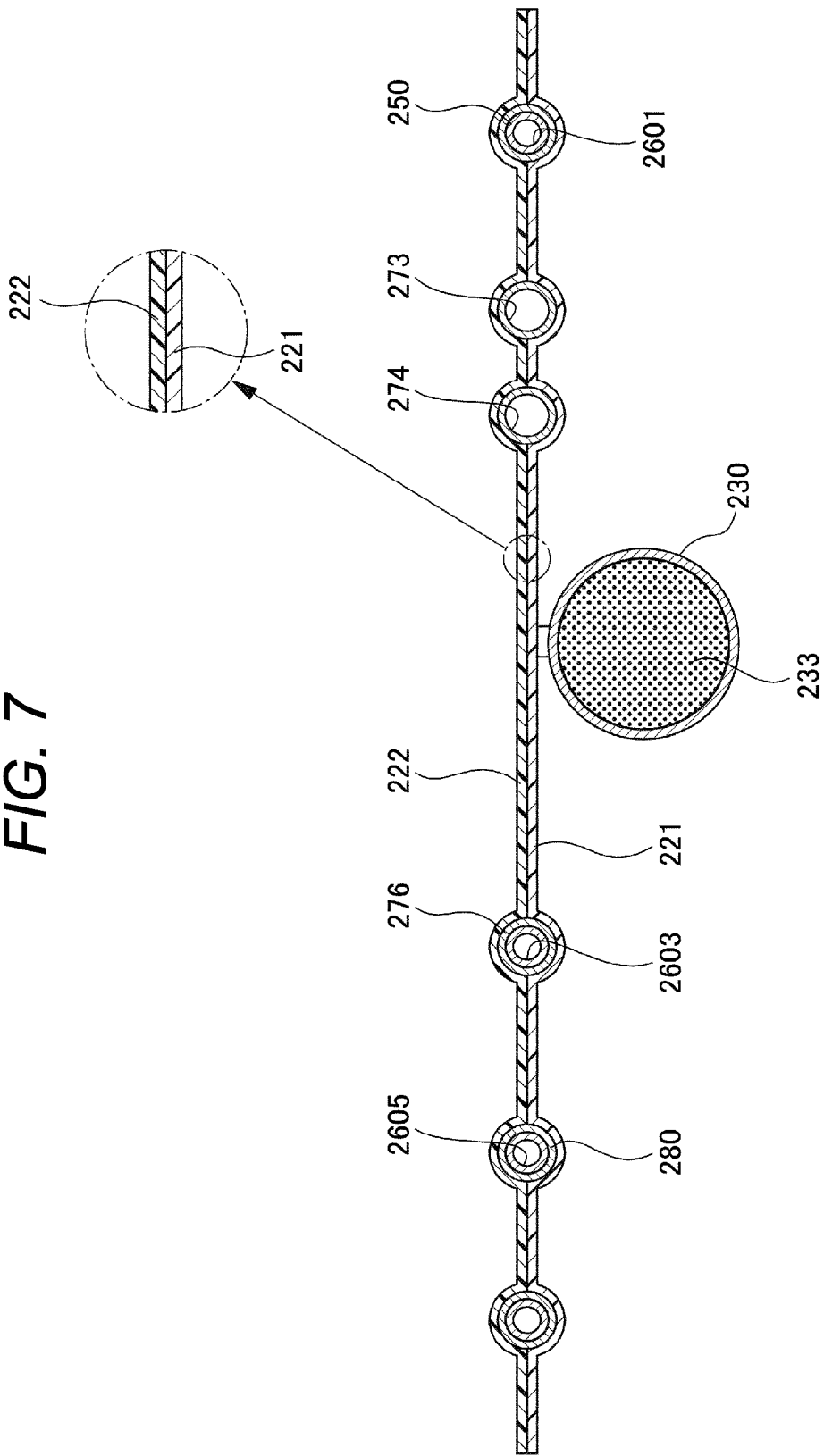
FIG. 7 is a cross sectional view along line A-A of FIG. 6.

According to the second and third examples, the hollow molded article 101 of the first example is applied to a blood purification circuit panel. In the following description, the second example refers to an example concerning matters relating to a panel, a flow channel, and a connection portion for external connection. The third example refers to an example concerning matters relating to installation of a dialyzer to a panel. FIG. 6 is a front view illustrating a blood purification circuit panel 210 according to the second and third examples. FIG. 7 is a cross sectional view along line A-A of FIG. 6.

The blood purification circuit panel 210 illustrated in FIG. 6 includes a board-like panel 220 which is disposed vertically with respect to the ground. The panel 220 has a rectangular shape with a horizontal width slightly greater than the vertical width.

The panel 220 is formed of two sheets of resin material (indicated at signs 221 and 222 in FIG. 7) which are affixed to each other, as will be seen from subsequent descriptions. The panel 220 has hollow flow channels formed at the interface of the sheets, between which tubes or coupling pipes (inserts) are sandwiched.

At substantially the center of the panel 220, a dialyzer 230 is attached. The dialyzer 230 is mounted to the panel 220 from one surface of the panel (the forward surface in the drawing). The dialyzer 230 is tubular in shape and attached to the panel 220 with the longitudinal direction of the dialyzer aligned with the vertical direction. The length of the dialyzer 230 is slightly greater than the vertical width of the panel 220. The dialyzer 230 is attached in such a way that its ends protrude respectively above and below the upper and lower sides of the panel 220.

A schematic configuration of the dialyzer 230 will be described. The tubular dialyzer 230, of which both ends are sealed, is configured so that blood can flow in via a blood inlet pipe portion 231 on the upper-end surface thereof, and purified blood can be discharged via a blood discharge pipe portion 232 on the lower-end surface thereof. In the dialyzer 230, a plurality (8,000 to 20,000) of thin pipes of artificial membrane (indicated at sign 233 in FIG. 7) are disposed along the axial direction of the dialyzer 230. The dialyzer 230 is configured so that blood can flow into the thin pipes 233.

The dialyzer 230 is also configured as follows. Dialysate is caused to flow in via a dialysate inlet pipe portion (circulation pipe portion) 234 on the lower-end side of the dialyzer 230. The dialysate is discharged via a dialysate discharge pipe portion (circulation pipe portion) 235 on the upper-end side. The dialysate flows outside the thin pipes 33 in the dialyzer 230. Accordingly, substances are exchanged between the blood and dialysate via the membrane of the thin pipes 233. Unwanted substances move into the dialysate, while useful substances move into the blood.

Figure 8:
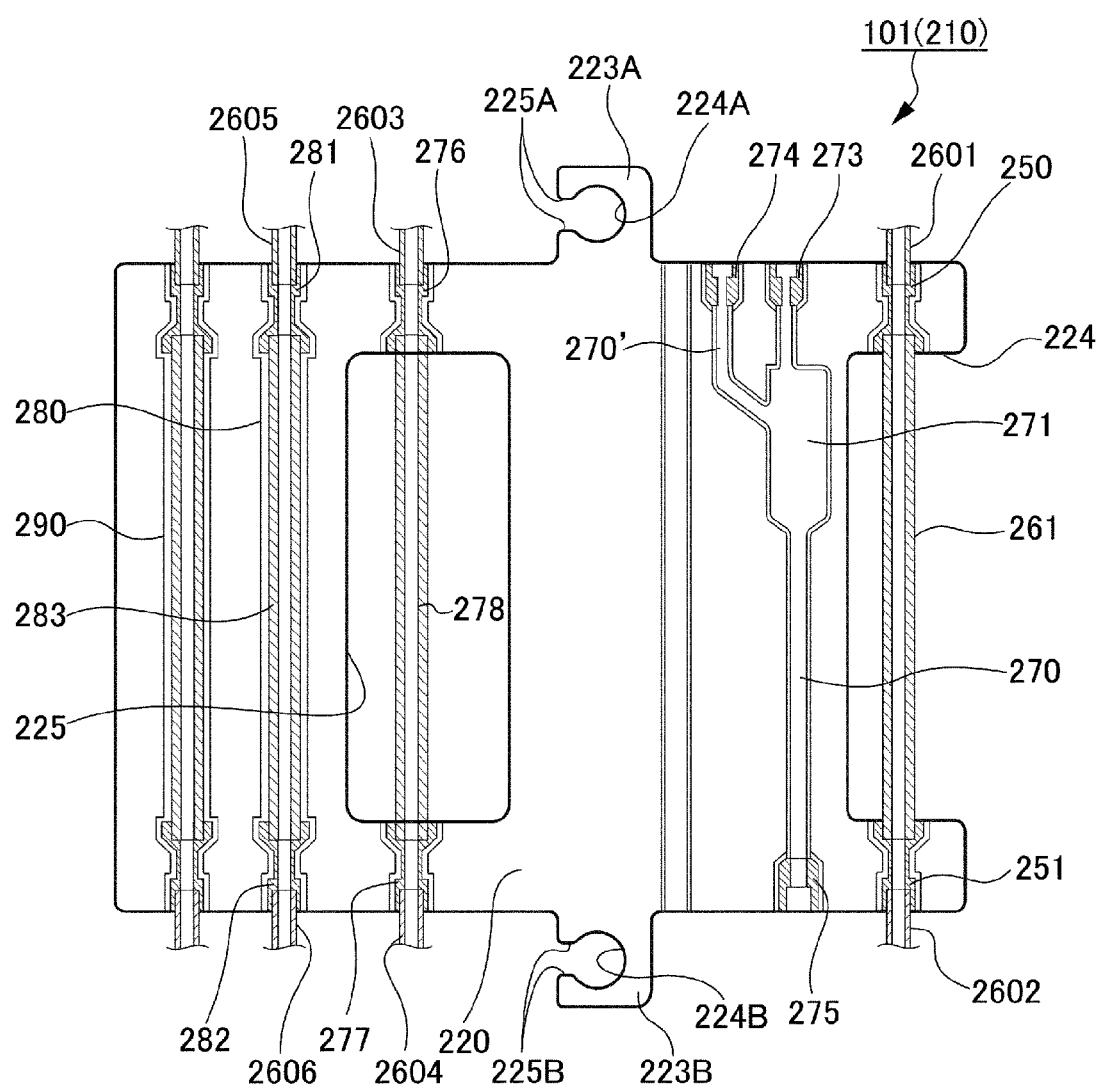
FIG. 8 is a cross sectional view of a section at the boundary of sheets of a panel.

The dialyzer 230 is attached to the panel 220 as follows. FIG. 8 illustrates the panel 220 to which the dialyzer 230 of FIG. 6 is yet to be attached. The panel 220 includes, at substantially the center of the upper side thereof, an attachment section 223A extending vertically upward. The attachment section 223A includes a cut-out 224A which is cut out of one of the vertical sides of the attachment section in a horizontal direction. The cut-out 224A has an inner peripheral portion on the bottom side opposite from the opening side, the inner peripheral portion having a semi-circular arch shape. The cut-out 224A has a shape including a pair of narrowing portions (such as convex portions) 225A. The narrowing portions 225A provide a narrow width of the cut-out 224A at mutually opposing inner peripheral portions on the opening side of the cut-out. Similarly, the panel 220 includes, at substantially the center of the lower side thereof, an attachment section 223B extending vertically downward. The attachment section 223B includes a cut-out 224B which is cut out in a horizontal direction. In this case, the cut-out 224B of the attachment section 223B is cut out in the same direction as the direction in which the cut-out 224A of the above-described attachment section 223A is cut out. FIG. 8 is a cross sectional view taken along the boundary of the sheets 221 and 222.

Figure 9:
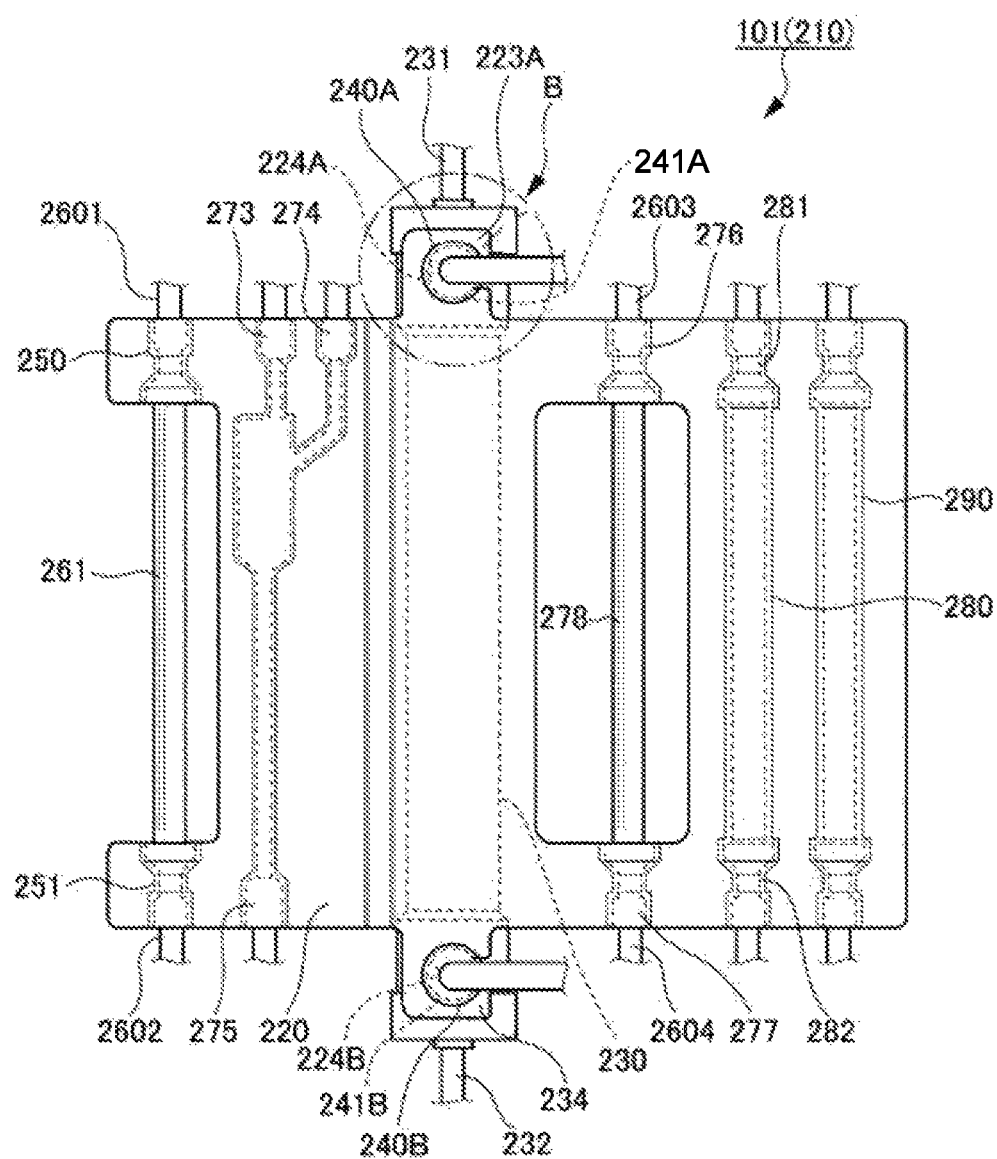
FIG. 9 is a back surface view illustrating the second and third examples of the blood purification circuit panel according to the present invention.

FIG. 9 is a back-side view of the blood purification circuit panel 210 of FIG. 6. Referring to FIG. 9, in the cut-out 24A of the attachment section 223A and the cut-out 224B of the attachment section 223B of the panel 220, a flange portion 240A and a flange portion 240B of the dialyzer 230 are respectively fitted. The flange portion 240A is formed around the pipe of the dialysate discharge pipe portion 235. The flange portion 240B is formed around the pipe of the dialysate discharge pipe portion 234.

Figure 10:
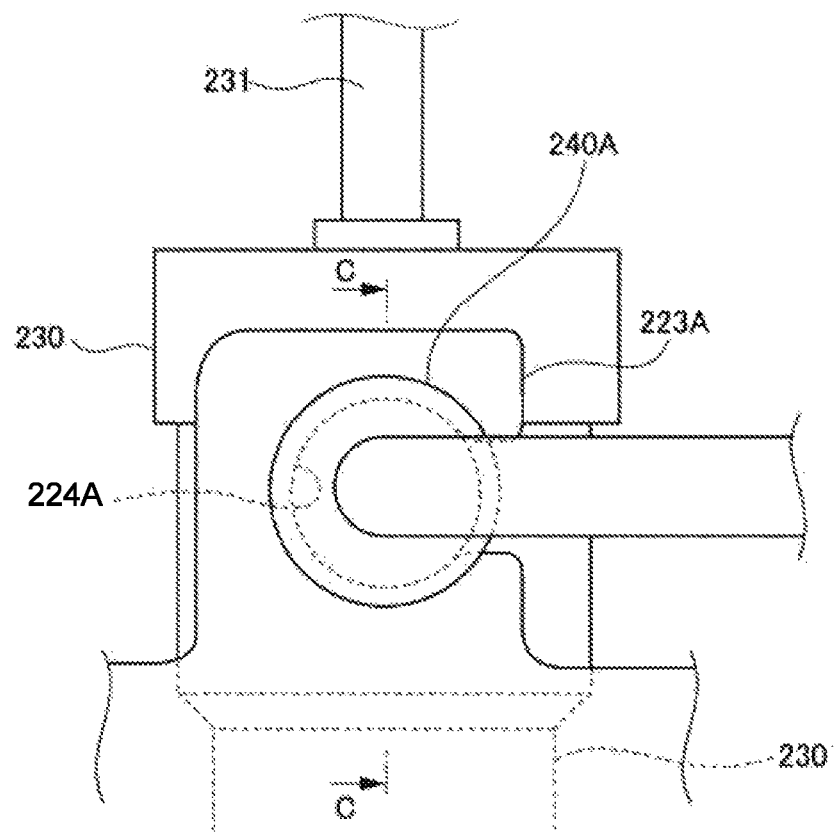
FIG. 10 is an enlarged view of an alternate-long-and-short-dash line portion B of FIG. 9.
Figure 11:
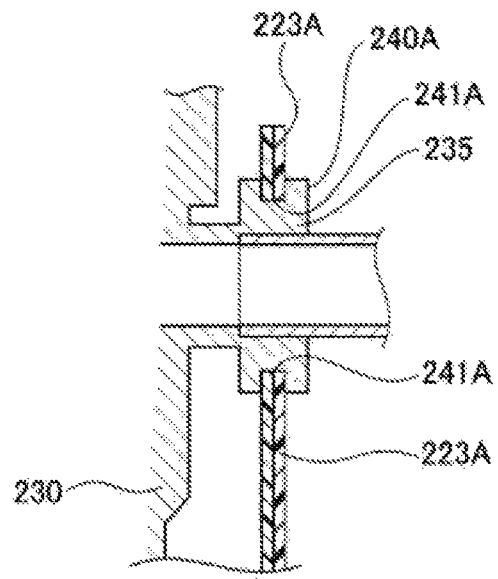
FIG. 11 is a cross sectional view along line C-C of FIG. 10.

FIG. 10 is an enlarged view of an alternate-long-and-short-dash line portion B of FIG. 9. Referring to FIG. 10, the flange portion 240A formed on the dialysate discharge pipe portion 235 is formed of circular sheet material. The flange portion 240A is formed so as to have a maximum diameter which is slightly greater than the diameter of the cut-out 224A of the attachment section 223A. FIG. 11 is a cross sectional view along line C-C of FIG. 10. Referring to FIG. 11, the flange portion 240A has a certain thickness and includes, in the center of the circumferential side surface thereof, an annular groove 241A along the circumferential direction. The flange portion 240A and the cut-out 224A of the attachment section 223A are configured such that the inner peripheral portion of the cut-out 224A of the attachment section 223A fits in the annular groove 241. The cut-out 224B of the attachment section 223B and the flange portion 240B have the same configuration illustrated in FIG. 10. The attachment section 223B is formed on the lower side of the panel 220. The flange portion 240B is formed on the dialysate inlet pipe portion 234 of the dialyzer 230.

In this configuration, the dialyzer 230 is secured to the panel 220 as follows. The inner peripheral portions of the cut-outs 224A and 224B of the corresponding attachment sections 223A and 223B of the panel 220 are engaged in the annular grooves 241A and 241B of the flange portions 240A and 240B of the dialyzer 230. The flange portions 240A and 240B are fitted in the cut-outs 224A and 224B across the narrowing portions 225A and 225B. In this way, the flange portions 240A and 240B fitted in the cut-outs 224A and 224B are configured so as not to easily disengage from the cut-outs 224A and 224B, thanks to the provision of the narrowing portions 225A and 225B. The flange portions 240A and 240B have the inner peripheral portions of the cut-outs 224A and 224B of the attachment sections 223A and 223B engaged in the annular grooves 241A and 241B, whereby axial displacement of the flange portions is regulated. Accordingly, the dialyzer 230 can be easily and reliably attached to the panel 220.

Referring back to FIG. 6, the panel 220 includes a cut-out portion 224 which is cut out a little toward the dialyzer 230 in a region on one side with respect to the dialyzer 230 (the right side in the figure), such as at the center of the lateral side of the region. The reduced-width portions of the panel 220 at the top and bottom of the cut-out portion 224 respectively include a coupling portion (first coupling portion) 250 and a coupling portion (second coupling portion) 251 made of resin material. The coupling portions constitute connection portions for external connection. The coupling portion 250 and coupling portion 251 communicate with a hollow flow channel 270 which will be described later, and are recessed inwardly from the peripheral edge of the disposed panel 220. The coupling portions have opening portions at the tip ends thereof and have a recessed pipe shape. The coupling portions are sandwiched between the sheets 221 and 222 of the panel 220 (see FIG. 7) and disposed coaxially. The coupling portion 250, as illustrated in FIG. 12 which is an enlarged view, is configured to enable the insertion of an externally attached tube (second tube) 2601 on the upper side of the panel 220, and configured to enable the insertion of a pump tube (first tube) 261 on the cut-out portion 224 side.

Figure 12:
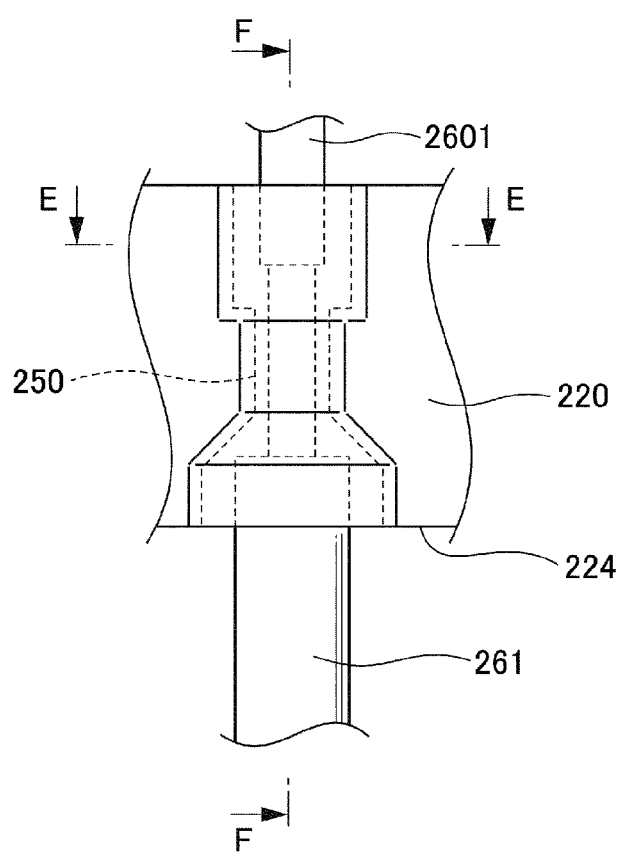
FIG. 12 is a plan view of a coupling portion used in the hollow molded article (blood purification circuit panel) according to the present invention.
Figure 13A:
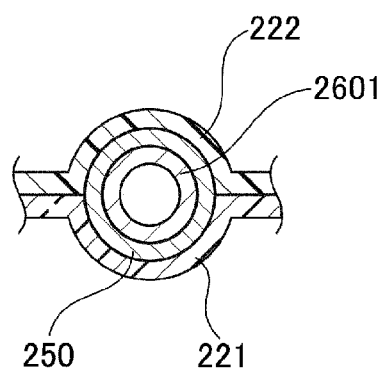
FIG. 13(a) shows a cross sectional view along line E-E of FIG. 12.
Figure 13B:
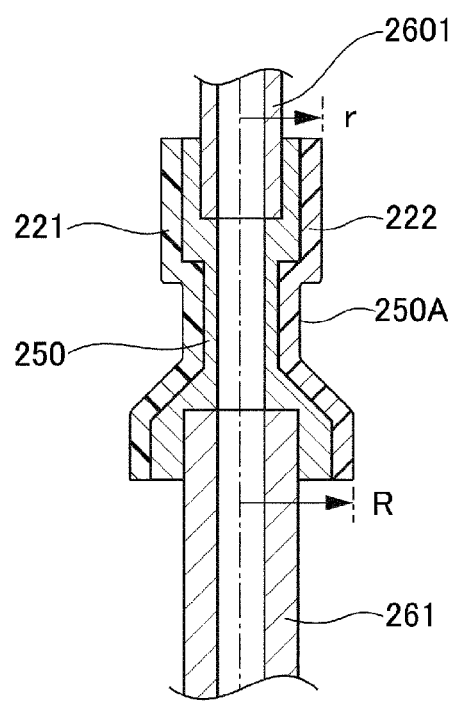
FIG. 13(b) is a cross sectional view along line F-F of FIG. 12.

FIG. 13(a) is a cross sectional view along line E-E of FIG. 12. FIG. 13(b) is a cross sectional view along line F-F of FIG. 12. As illustrated in FIG. 13(b), the coupling portion 250, on the externally attached tube 2601 side, has a small outer diameter r and an inner diameter which enables the insertion of the externally attached tube 2601. On the pump tube 261 side, the coupling portion 250 has a large outer diameter R and an inner diameter enabling the insertion of the pump tube 261. The coupling portion 250 has a shape which includes a constriction 250A at substantially the center in the axial direction thereof. The coupling portion 250 having such shape is sandwiched between the sheets 221 and 222, and is disposed with the central axis thereof positioned in the plane including the panel 220, providing the effect that axial displacement of the coupling portion 250 can be reliably regulated. The coupling portion 251 has substantially the same configuration as the coupling portion 250, with the large diameter side of the coupling portion 251 disposed on the cut-out portion 224 side of the panel 220, and the small diameter side thereof disposed on the lower side of the panel 220. The coupling portion 251 is configured to enable insertion of an externally attached tube (third tube) 2602 on the lower-side end surface of the panel 220.

Figure 14:
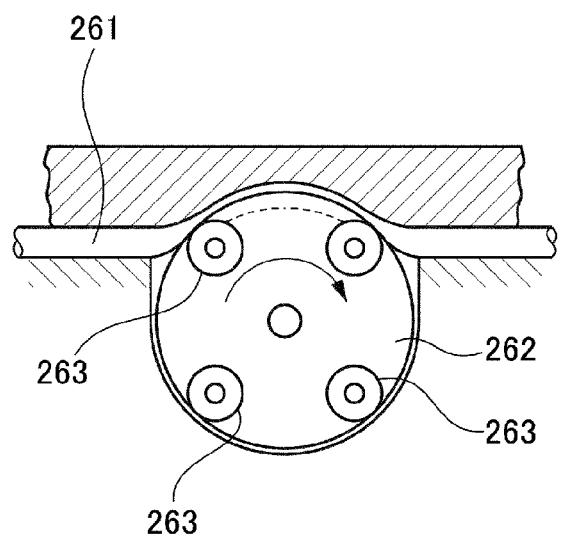
FIG. 14 is a schematic view schematically illustrating a tube pump.

Accordingly, as illustrated in FIG. 6, the pump tube 261 can be disposed in the cut-out portion 224 of the panel 220. The pump tube 261 is a constituent member of a tube pump. The tube pump is configured to drive the pump tube to deliver the fluid in the pump tube 261 in one direction. Accordingly, blood or dialysate delivered from the pump tube can be sent into the dialyzer 230 via the blood inlet pipe portion 231 or dialysate inlet pipe portion 234. FIG. 14 is a schematic view of the tube pump. Referring to FIG. 14, a rotating body 262 is disposed adjacent to the pump tube 261. The rotating body 262 includes a plurality of (such as four) rollers 263 along the circumferential direction thereof. As the rotating body 262 rotates, the rollers 263 are moved in one direction while successively pressing a part in a longitudinal direction of the pump tube 261. As a result, the fluid in the pump tube 261 is delivered in the same direction by a negative pressure generated in the pump tube 261.

Figure 15:
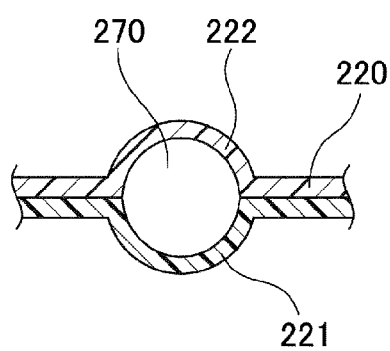
FIG. 15 is a cross sectional view along line G-G of FIG. 6.

Referring back to FIG. 6, in a region of the panel 220 between the pump tube 261 and the dialyzer 230, the panel 220 includes a hollow flow channel 270 extending from the upper side to the lower side of the panel. The hollow flow channel 270, as illustrated in FIG. 15 showing a cross sectional view along line G-G of FIG. 6, may be configured as follows. The panel 220 includes the two sheets 221 and 222 affixed to each other. One sheet 221 has a recessed portion (with a semi-circular arched cross section, for example) which is formed in a region defining the hollow flow channel 270 so as to provide a gap from the other sheet 222. The other sheet 222 has a recessed portion (with a semi-circular arched cross section, for example) which is formed in a region defining the hollow flow channel 270 so as to provide a gap from the one sheet 221.

The hollow flow channel 270 includes a hollow chamber 271 at a point along the path thereof, the hollow chamber 271 having a relatively large region as viewed in plan. The hollow flow channel 270 includes another hollow flow channel 270' extending from the hollow chamber 271 to one side (such as the upper side in FIG. 6) of the panel 220. Accordingly, the hollow flow channels 270 and 270' are configured to serve as diverting flow channels or converging flow channels by changing the flow of fluid.

The coupling portion 273 (see FIG. 7), the coupling portion 274 (see FIG. 7), and the coupling portion 275 are sandwiched between the sheets 221 and 222 (see FIG. 7) and disposed at the ends of the hollow flow channels 270 and 270' in the plane of the panel 220. The coupling portions include pipe members disposed coaxially with the hollow flow channels 270 and 270'. The end faces of the coupling portion 273, coupling portion 274, and coupling portion 275 which are substantially flush with the upper side and lower side of the panel 220 include inner diameters adapted for insertion of externally attached tubes (not illustrated).

As illustrated in FIG. 6, the panel 220 includes, in a region on the other side with respect to the dialyzer 230 (left side in the figure), an opening portion 225 adjacent to the dialyzer 230. The reduced-width portions of the panel 220 at the top and bottom of the opening portion 225 respectively include a coupling portion (first coupling portion) 276 and a coupling portion (second coupling portion) 277. The coupling portion 276 has substantially the same configuration as the coupling portion 250. The coupling portion 277 has substantially the same configuration as the coupling portion 251. The coupling portions 276 and 277 are sandwiched between the sheets 221 and 222 of the panel 220 (see FIG. 7).

In the opening portion 225 of the panel 220, a pump tube (first tube) 278 is disposed. One end of the pump tube 278 is inserted into the coupling portion 276. The other end of the pump tube 278 is inserted into the coupling portion 277. The coupling portion 276 is configured to enable insertion of an externally attached tube (second tube) 2603 into the end face thereof on the upper side of the panel 220. The coupling portion 77 is configured to enable insertion of an externally attached tube (third tube) 2604 into the end face thereof on the lower side of the panel 220. The pump tube 278 is a constituent member of a tube pump, similarly to the above-described pump tube 261. The tube pump is configured to deliver the fluid in the pump tube 278 in one direction by the driving of the tube pump. Accordingly, blood or dialysate delivered via the pump tube can be sent into the dialyzer 230 via the blood inlet pipe portion 231 or the dialysate inlet pipe portion 234.

In a region of the panel 220 on the outer side than the pump tube 278, hollow flow channels 280 and 290 are disposed in parallel, extending from the upper side to the lower side of the panel 220. The hollow flow channels 280 and 290 have the same configuration.

The hollow flow channel 280, compared with the above-described hollow flow channel 270, is a linear flow channel which does not have a diverting flow channel or a converging flow channel. A coupling portion (first coupling portion) 281 and a coupling portion (second coupling portion) 282 respectively formed on the upper side and the lower side of the panel 220 have substantially the same configuration as the coupling portion 250, including the central constriction. As illustrated in FIG. 8, the coupling portion 281 and the coupling portion 282 are coupled by means of a tube (first tube) 283 made of resin material. The tube 283 is sandwiched, together with the coupling portion 281 and the coupling portion 282, between the sheets 221 and 222. Accordingly, the hollow flow channel 280 has an inner diameter greater than the inner diameter of the hollow flow channel 270 so as to be adapted to the large outer diameter of the ends of the coupling portion 281 and coupling portion 282. The coupling portion 281 has an externally attached tube (second tube) 2605 inserted thereinto. The coupling portion 282 has an externally attached tube (third tube) 2606 inserted thereinto.

Thus, in the blood purification circuit panel 210 with the above-described configuration, a blood purification circuit including the dialyzer 230, the tube pumps and the like can be configured (mounted) on the panel 220 using the externally attached tubes.

While it has been described that the sheet 221, the sheet 222, the coupling portions and the like are formed of resin material, the material may be selected from, for example, polyolefins such as polyethylene and polypropylene; styrene-based resins such as acrylonitrile-butadiene-styrene (ABS), styrene-butadiene copolymer (SBC), and polystyrene; polycarbonate; polymethylmethacrylate resin (PMMA); vinyl chloride resin; styrene-based elastomer; fluorine resin; and polysulfone.

Preferably, the coupling portions 250, 251 are formed of resin material in advance by injection molding and the like so as to be capable of adhering to tubes, and then integrally welded and fixed in a state of being sandwiched between the sheets 221 and 222. Accordingly, the resin material contained in the coupling portions may be selected from, for example, polycarbonate; vinyl chloride resin; acrylonitrile-butadiene-styrene (ABS); and polymethylmethacrylate resin (PMMA).

(First Modification)

Figure 16:
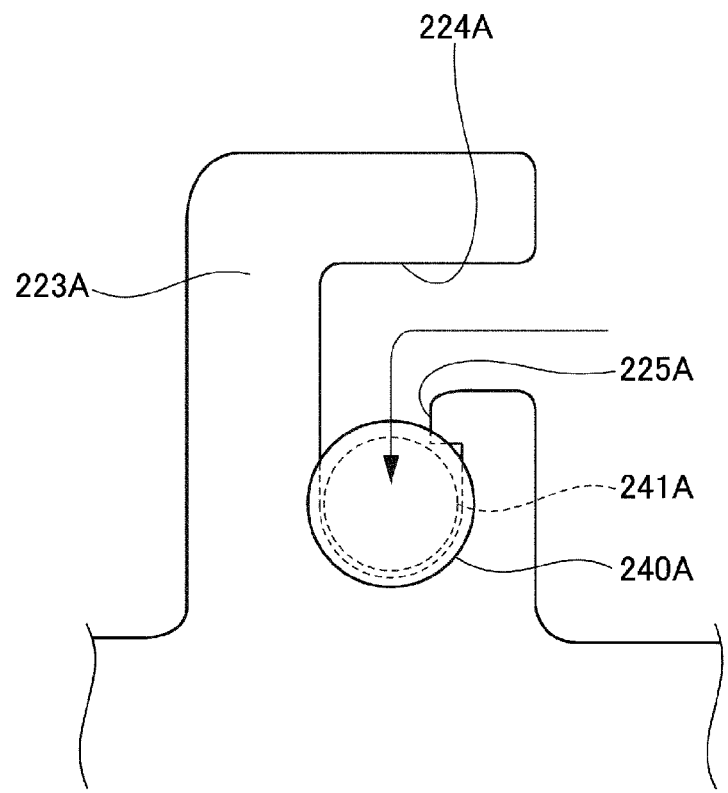
FIG. 16 is a configuration diagram of a first modification of an attachment portion of the panel and the dialyzer.

In the panel 220 according to the second or third example, the cut-outs 224A and 224B formed in the attachment sections 223A and 223B have the shape where the vertical side is cut out in the horizontal direction. However, the attachment section 223A, for example, may have a shape illustrated in FIG. 16. Specifically, as illustrated in FIG. 16, the cut-out 224A may have a shape where the attachment section 223A is cut on a vertical side in the horizontal direction and additionally cut vertically downward, forming an inverted-L shape. The cut-out 224A formed by the cutting in the vertically downward direction has a semi-circular arched inner peripheral portion on the bottom side. At the bend portion bending from the horizontal direction into the vertically downward direction, a narrowing portion 225A is formed whereby the width of the cut-out is narrowed.

In this configuration, too, the inner peripheral portion of the cut-out 224A of the attachment section 223A is engaged in the annular groove 241A of the flange portion 240A, and the flange portion 240A is fitted in the cut-out 224A across the narrowing portion 225A. In this way, the flange portion 240A fitted in the cut-out 224A is configured so as not to be easily detached from the cut-out 224A, thanks to the provision of the narrowing portion 225A.

(Second Modification)

Figure 17:
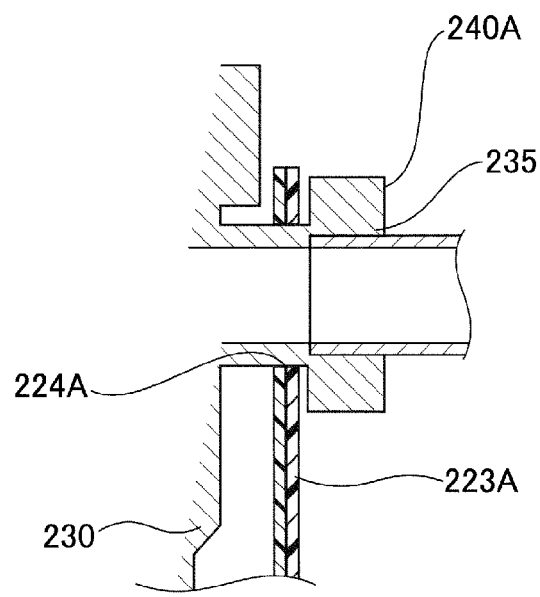
FIG. 17 illustrates a second modification of the present invention, drawn in a manner corresponding to FIG. 11.

In the second or third example, the panel 220 is configured such that the dialysate inlet pipe portion 234 and the dialysate discharge pipe portion 235 of the dialyzer 230 are attached to the attachment sections 223A and 223B via the flange portions 240A and 240B. However, such configuration is not a limitation. For example, the panel 220 may be configured such that the dialysate inlet pipe portion 234 and the dialysate discharge pipe portion 235 are attached where the flange portions 240A and 240B are not formed. FIG. 17 illustrates the second modification drawn in a manner corresponding to FIG. 11.

As illustrated in FIG. 17, the attachment section 223A of the panel 220 is configured so as to be fitted on the dialysate discharge pipe portion 235 between the dialyzer 230 and the flange portion 240A. In this case, the cut-out 224A of the attachment section 223A includes the narrowing portion 225A illustrated in FIG. 8, for example, and the panel 220 is configured such that the dialysate discharge pipe portion 235 is fitted into the cut-out 224A across the narrowing portion 225A of the attachment section 223A. The flange portion 240A prevents the attachment section 223A of the panel 220 from being detached from the dialysate discharge pipe portion 235.

(Third Modification)

Figure 18:
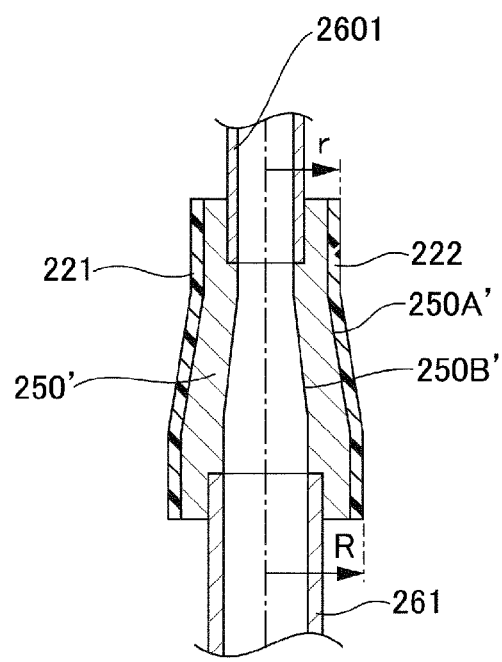
FIG. 18 illustrates a third modification of the present invention, drawn in correspondence to FIG. 13(b).

In the second or third example, the coupling portions (such as the coupling portion 250), as illustrated in FIG. 13(*b*), have a shape including the constriction 250A at substantially the center in the axial direction thereof. However, the shape of the coupling portions is not limited to such shape. For example, the coupling portions may have a shape such that the outer diameter of at least the outer peripheral surface thereof tapers from one end to the other. FIG. 18 illustrates the configuration of such a coupling portion. The coupling portion is drawn in a manner corresponding to FIG. 13(*b*). As illustrated in FIG. 18, the coupling portion 250' has a shape including tapers 250A' and 250B' where the outer and inner diameters are both decreasing from the pump tube 261 toward the externally attached tube 2601. The coupling portion 250' having such shape, when sandwiched between the sheets 221 and 222, provides the effect of reliably regulating axial displacement.

Fourth Example

Figure 19:
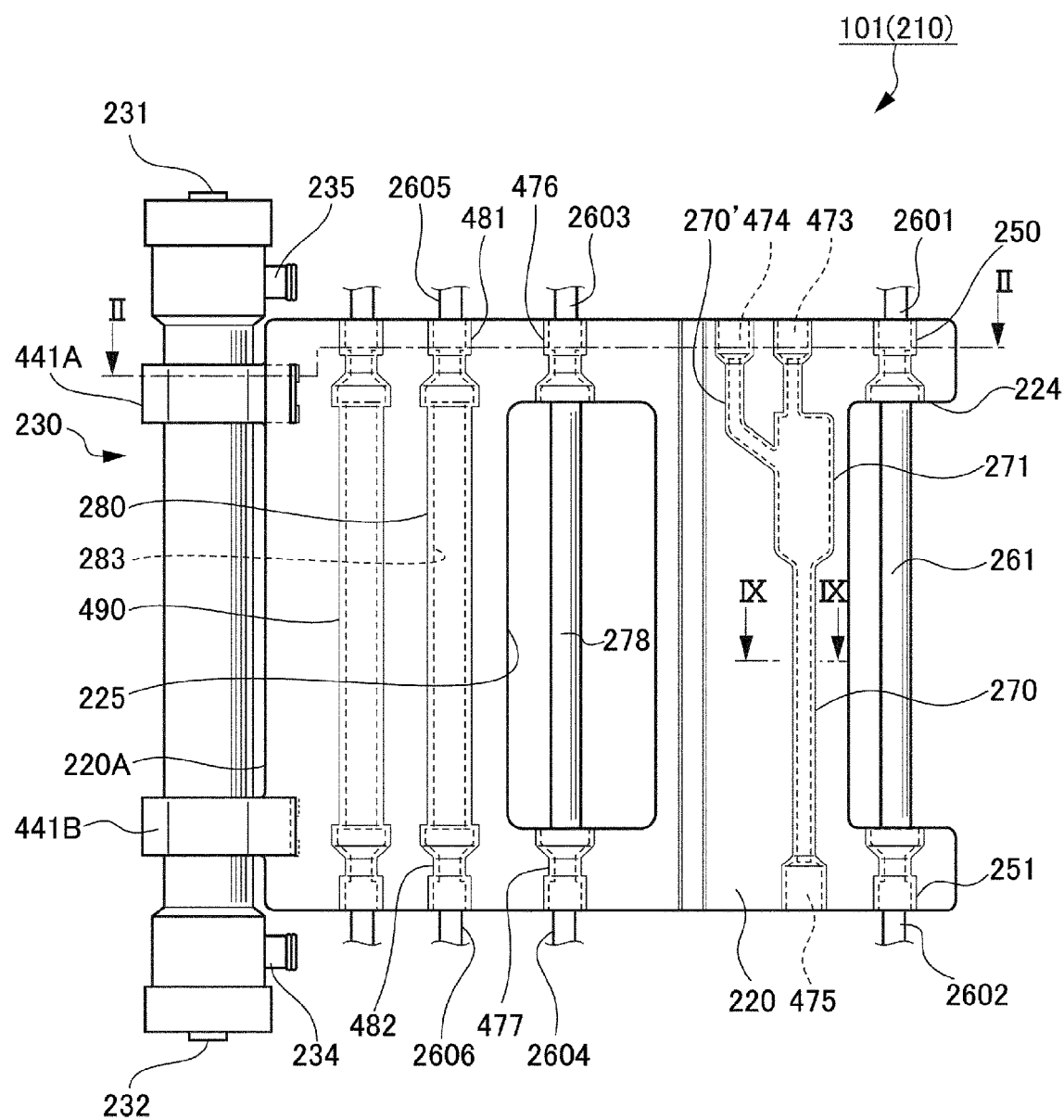
FIG. 19 is a front view illustrating the fourth example of the hollow molded article (blood purification circuit panel) according to the present invention.
Figure 20:
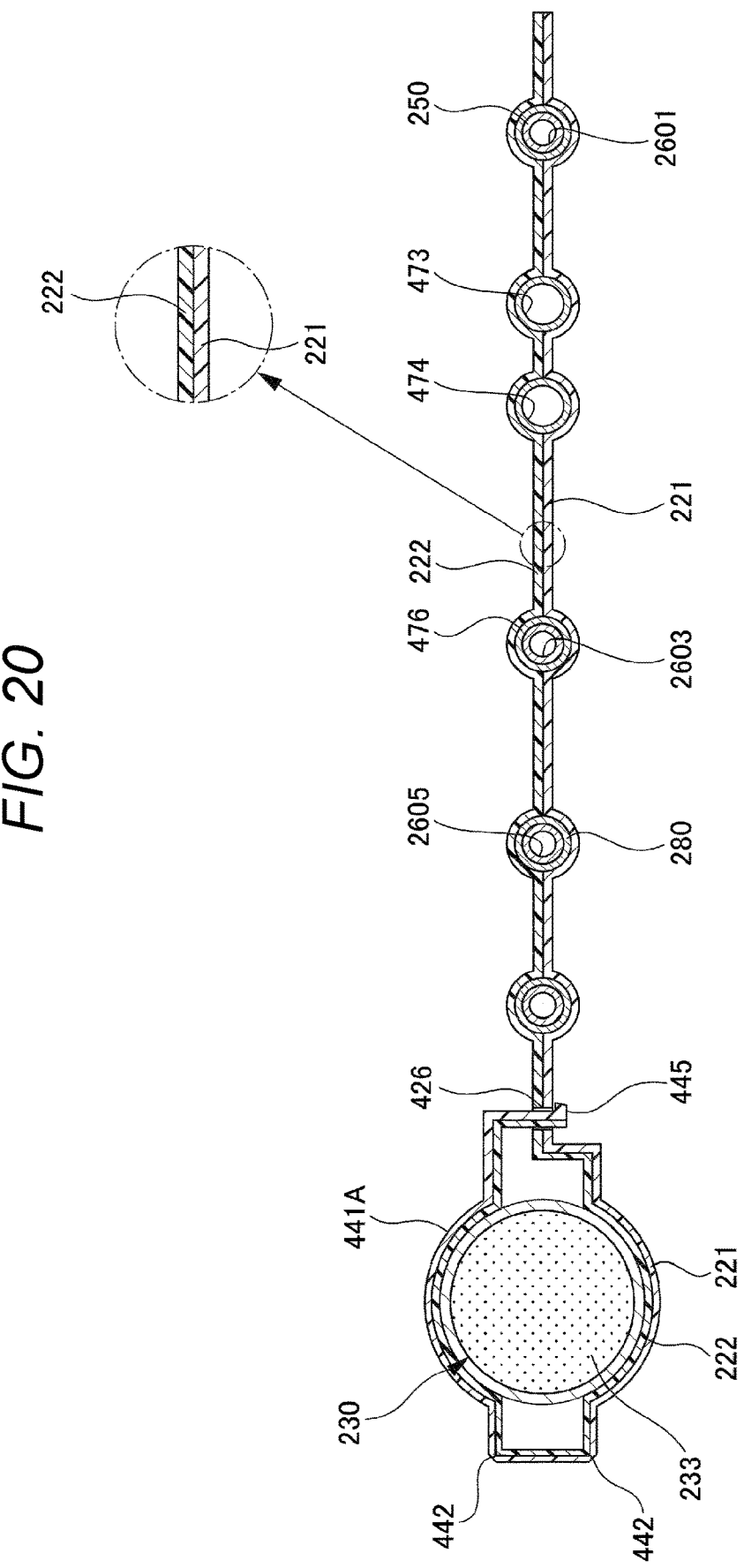
FIG. 20 is a cross sectional view along line II-II of FIG. 19.

The fourth example relates to the application of the hollow molded article 101 according to the first example to a blood purification circuit panel, as in the second and third examples. The fourth example herein refers to an example concerning matters relating to the mounting of a dialyzer to the panel differently from the third example. FIG. 19 is a front view illustrating the fourth example of the blood purification circuit panel. FIG. 20 is a cross sectional view along line II-II of FIG. 19.

The blood purification circuit panel 210 illustrated in FIG. 19 includes the board-like panel 220 disposed vertically with respect to the ground. The panel 220 has a rectangular shape with a horizontal width slightly greater than a vertical width.

The panel 220 includes two resin material sheets (indicated at signs 221, 222 in FIG. 20) affixed to each other, as will be described below. The panel 220 has hollow flow channels disposed at the interface of the sheets 221 and 222. In addition, the panel 220 is configured to sandwich tubes or coupling pipes (inserts) between the sheets.

The dialyzer 230 is attached adjacent to one side 220A of the panel 220, such as the left side in the figure. The dialyzer 230 has a cylindrical shape. The dialyzer 230 is disposed with its longitudinal direction parallel with the one side 220A. The dialyzer 230 has a length slightly greater than the vertical width of the panel 220. The dialyzer 230 is attached so as to protrude above the upper side and below the lower side of the panel 220 at the respective ends of the dialyzer. The dialyzer 230 is similar to the dialyzer of the third example. In the fourth example, however, the dialysate inlet pipe portion 234 and the dialysate discharge pipe portion 235 protrude from the dialyzer 230 toward the panel 220.

The dialyzer 230 having the above-described configuration is configured to be attached to the panel 220 via securing bands 441A and 441B formed on one side 220A of the panel 220. The securing bands 441A and 441B are disposed at an interval along the longitudinal direction of the dialyzer 230. The securing band 441A is disposed in the vicinity of the dialysate discharge pipe portion 235. The securing band 441B is disposed in the vicinity of the dialysate inlet pipe portion 234. The securing bands 441A and 441B, as illustrated in FIG. 20, are integrally formed (molded) with the panel 220 including the sheets 221 and 222.

The securing bands 441A and 441B, as illustrated in FIG. 21(*a*), are configured such that one end thereof can be fixed to a first surface of the panel 220 on the one side 220A, while the other end can be passed around the peripheral surface of the dialyzer 230 and locked onto a second surface of the panel 220 on the one side 220A. That is, the one end of the securing band 441A is fixed to the front surface on the one side 220A of the panel 220 as illustrated; the other end is passed around the peripheral surface of the dialyzer 230 and locked onto the back surface on the one side 220A of the panel 220 as illustrated. The one end of the securing band 441B is fixed to the back surface on the one side 220A of the panel 220 as illustrated; the other end is passed around the peripheral surface of the dialyzer 230 and locked onto the front surface on the one side 220A of the panel 220 as illustrated. Accordingly, the one ends are fixed to different surfaces of the panel 220 between the securing bands 441A and 441B, and the other ends are also locked onto different surfaces of the panel 220 between the securing bands. In this way, the dialyzer 230 can be attached to the panel 220 reliably.

Figure 21A:
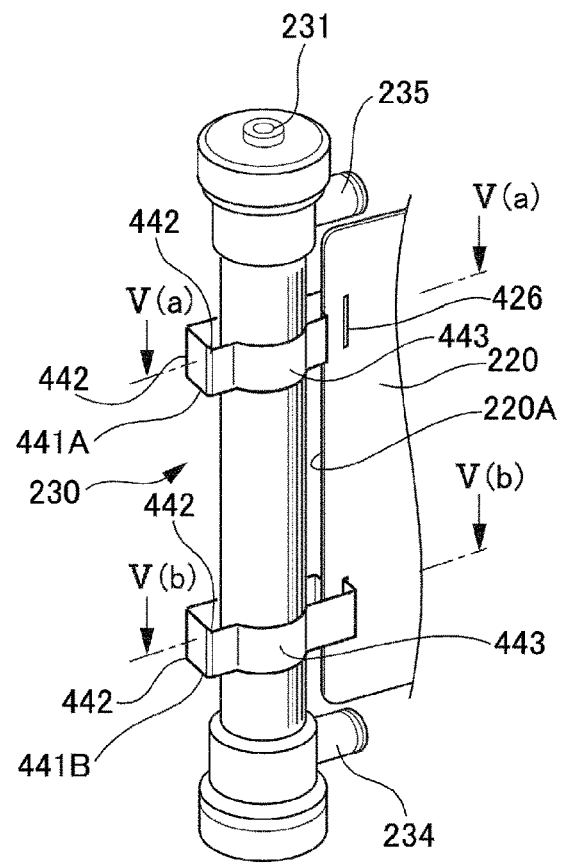
FIG. 21(a) illustrates securing bands being locked.
Figure 21B:
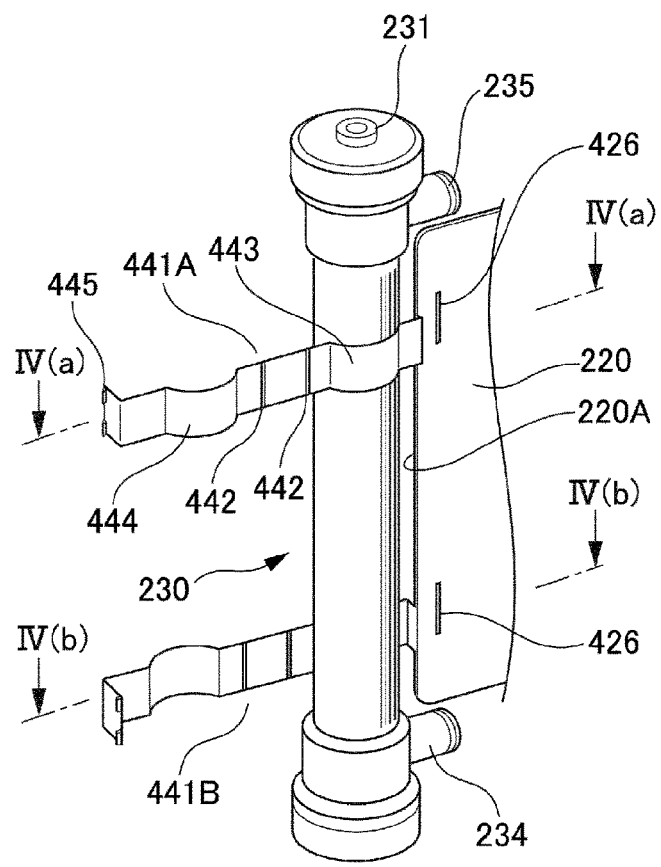
FIG. 21(b) illustrates the securing bands being unlocked.

FIG. 21(b) illustrates the other ends of the securing bands 441A and 441B detached from the panel 220. The securing band 441A, for example, has a pair of hinge portions 442 disposed in parallel at substantially the center between one and the other ends of the securing band. The hinge portions 442 may be provided by forming cuts at the illustrated portion along the width direction. The hinge portions 442 enable the securing band 441 to be bent in U-shape, as illustrated in FIG. 21(a). In this way, the dialyzer 230 can be sandwiched by the securing band 441. The securing band 441A includes arched surfaces 443 and 444 between one end of the band and the hinge portions 442 and between the hinge portions 442 and the other end, the arched surfaces having substantially the same curvature as the outer peripheral surface of the dialyzer 230. Accordingly, the dialyzer 230 can be sandwiched in a closely contacted manner. In addition, the other end of the securing band 441A is bent substantially at a right angle, with a hook 445 disposed at the tip end of the other end. The securing band 441A is configured such that when the securing band 441A is bent in U-shape so as to sandwich the dialyzer 230, the hook 445 can be locked in a slit (engaging hole) 426 formed in the panel 220. The securing band 441B has the same configuration as the securing band 441A except for the surface fixed to the panel 220.

Figure 22A:
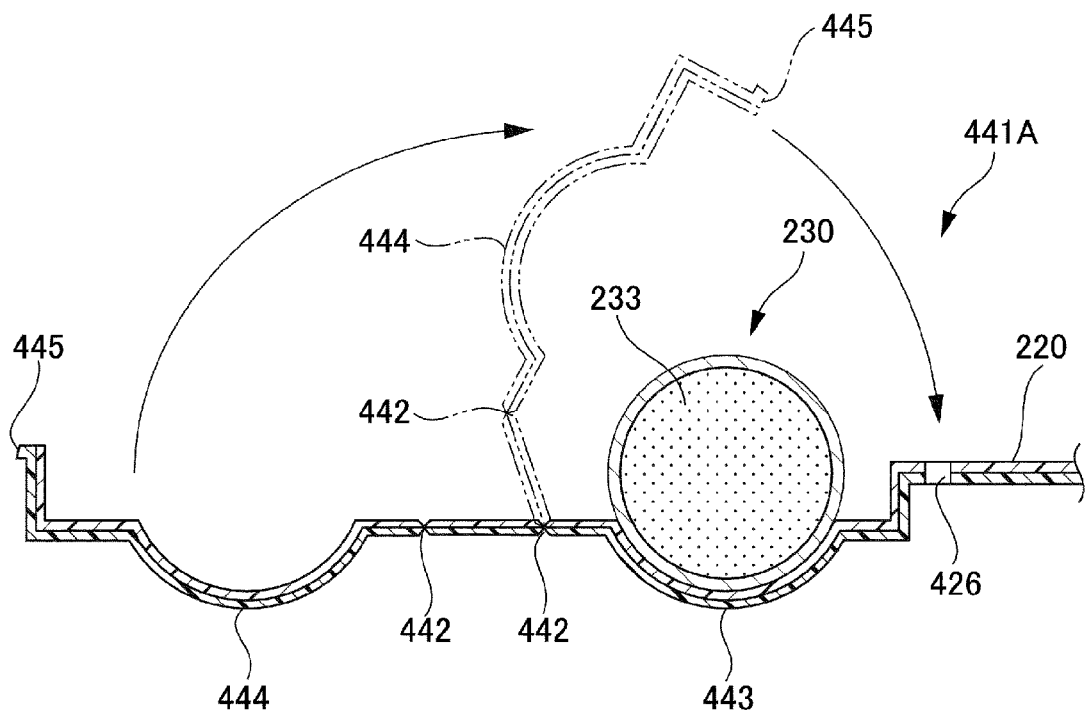
FIG. 22(a) is a cross sectional view along line IV(a)-IV(a) of FIG. 21(b)
Figure 22B:
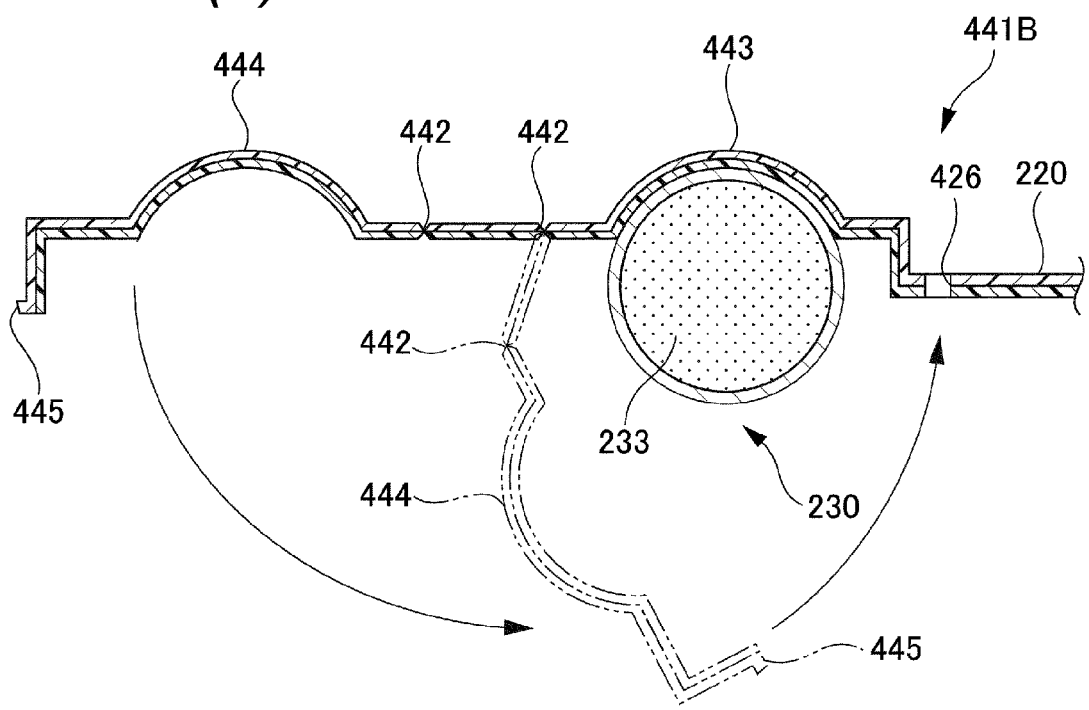
FIG. 22(b) is a cross sectional view along line IV(b)-IV(b) of FIG. 21(b).

FIGS. 22(a) and (b) are cross sectional views respectively taken along line IV(a)-IV(a) and line IV(b)-IV(b) of FIG. 21(b). With regard to the securing band 441A, as illustrated in FIG. 22(a), after the dialyzer 230 is abutted on the arched surface 443, the other end of the securing band 441A where the hook 445 is formed is moved as indicated by arrows, thus bending the securing band 441A at the hinge portions 442. In this way, the dialyzer 230 can be sandwiched. Similarly, with regard to the securing band 441B, as illustrated in FIG. 22(b), after the dialyzer 230 is abutted on the arched surface 443, the other end of the securing band 441B (where the hook 445 is formed) is moved as indicated by arrows, thus bending the securing band at the hinge portions 442. In this way, the dialyzer 230 can be sandwiched.

Figure 23A:
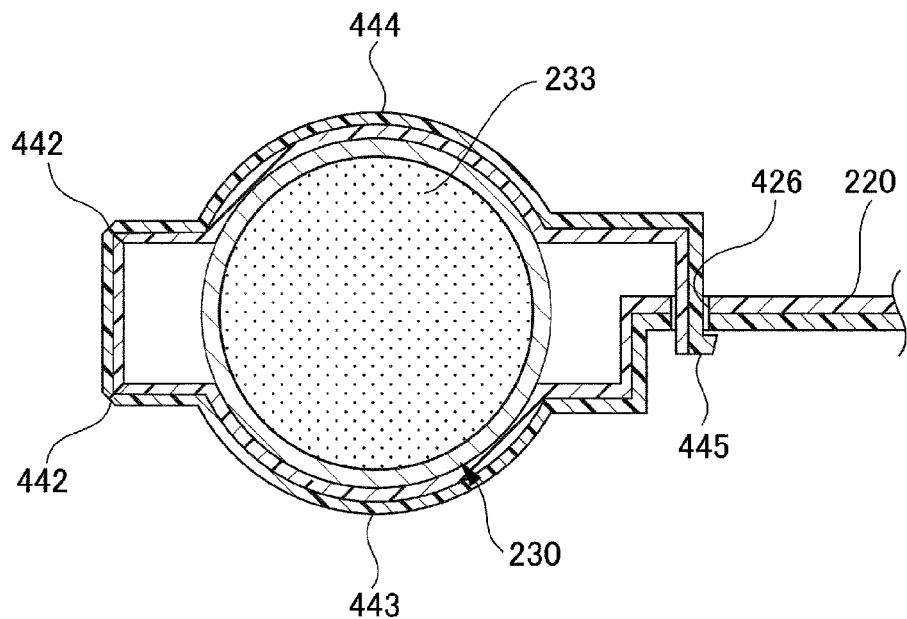
FIG. 23(a) is a cross sectional view along line V(a)-V(a) of FIG. 21(a)
Figure 23B:
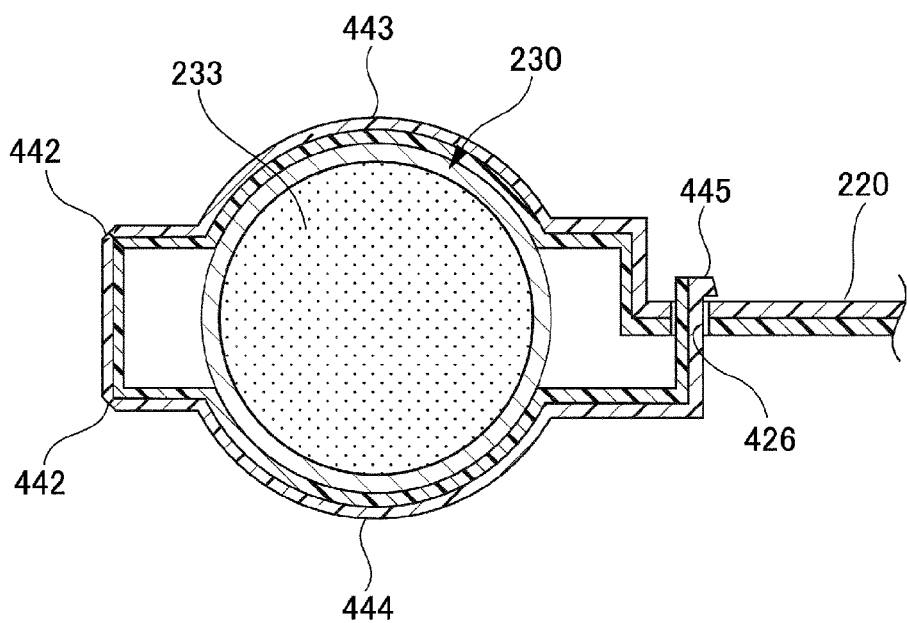
FIG. 23(b) is a cross sectional view along line V(b)-V(b) of FIG. 21(a).

FIGS. 23(a) and (b) are respectively cross sectional views along line V(a)-V(a) and line V(b)-V(b) of FIG. 21(a). With regard to the securing band 441A, as illustrated in FIG. 23(a), the arched surface 444 abuts on the dialyzer 230, with the other end where the hook 445 is formed locked in a slit 426 of the panel 220. With regard to the securing band 441B, as illustrated in FIG. 23(b), the arched surface 444 abuts on the dialyzer 230, with the other end where the hook 445 is formed locked in a slit 426 of the panel 220. Accordingly, the dialyzer 230 can be reliably attached to the panel 220 via the securing bands 441A and 441B.

The securing bands 441A and 441B may be configured such that friction material (not illustrated) is affixed to at least the surfaces of the arched surfaces 443 and 444 that abut on the dialyzer 230. In this case, axial movement of the dialyzer 230 sandwiched by the securing bands 441A and 441B can be prevented by the friction material.

The size of the panel 220 may be set so that the upper side and lower side of the panel 220 are respectively positioned proximate to the dialysate inlet pipe portion 234 and the dialysate discharge pipe portion 235 of the dialyzer 230. In this case, too, axial movement of the dialyzer 230 can be prevented.

Referring back to FIG. 19, the opposite side from the one side 220A, to which the dialyzer 230 is attached, has a cut-out portion 224 at the center which is cut out toward the dialyzer 230. The reduced-width portions of the panel 220 at the top and bottom of the cut-out portion 224 respectively include a first coupling portion 250 and a second coupling portion 251 made of resin material and constituting connection portions for external connection. The first coupling portion 250 and the second coupling portion 251 include pipe members. The coupling portions are sandwiched between the sheets 221 and 222 of the panel 220 (see FIG. 20) and coaxially disposed. The configuration of the first coupling portion 250 is the same as described with reference to the second and third examples (see FIG. 12 and FIGS. 13(a)(b)).

Accordingly, as illustrated in FIG. 19, the pump tube 261 can be disposed in the cut-out portion 224 of the panel 220. The pump tube 261 is a constituent member of a tube pump. The tube pump is configured to deliver fluid in the pump tube 261 in one direction by driving the pump tube. Accordingly, blood or dialysate delivered via the pump tube can be sent into the dialyzer 230 via the blood inlet pipe portion 231 or the dialysate inlet pipe portion 234. The tube pump is generally the same as the tube pump (see FIG. 14) described with reference to the second and third examples.

Referring back to FIG. 19, the panel 220 includes, in a region adjacent to the pump tube 261, a hollow flow channel 270 extending from the upper side to the lower side of the panel 220. The cross section of the hollow flow channel 70 along line IX-IX in FIG. 19 is the same as described in the second and third examples illustrated in FIG. 9 (see FIG. 15).

The hollow flow channel 270 includes, at a point along the path thereof, a hollow chamber 271 having a relatively large region as viewed in plan. From the hollow chamber 271 to one side of the panel 220 (such as the upper side in FIG. 19), another hollow flow channel 270' is provided. Accordingly, the hollow flow channels 270 and 270' can be configured as diverting flow channels or converging flow channels by changing the flow of the fluid.

A third coupling portion 473 (see FIG. 20), a fourth coupling portion 474 (see FIG. 20), and a fifth coupling portion 475 are sandwiched between the sheets 221 and 222 (see FIG. 20) and disposed at the respective ends of the hollow flow channels 270 and 270' in the plane of the panel 220. These coupling portions include pipe members coaxially disposed with the hollow flow channels 270 and 270'. The end faces of the third coupling portion 473, the fourth coupling portion 474, and the fifth coupling portion 475 which are substantially flush with the upper side and lower side of the panel 220 have inner diameters for inserting externally attached tubes (not illustrated).

As illustrated in FIG. 19, the panel 220 includes an opening portion 225 in a region adjacent to the hollow flow channel 270. The reduced-width portions of the panel 220 at the top and bottom of the opening portion 225 respectively include a sixth coupling portion 476 and a seventh coupling portion 477. The sixth coupling portion 476 has substantially the same configuration as the first coupling portion 250. The seventh coupling portion 477 has substantially the same configuration as the second coupling portion 251. The sixth coupling portion 476 and the seventh coupling portion 477 are sandwiched between the sheets 221 and 222 of the panel 220 (see FIG. 20).

In the opening portion 225 of the panel 220, a pump tube 278 is disposed. One end of the pump tube 278 is inserted into the sixth coupling portion 476. The other end of the pump tube 278 is inserted into the seventh coupling portion 477. The sixth coupling portion 476 is configured for insertion of an externally attached tube 2603 into the end face thereof on the upper side of the panel 220. The seventh coupling portion 477 is configured for insertion of an externally attached tube 2604 into the end face thereof on the lower side of the panel 220. The pump tube 278 is a constituent member of a tube pump, similarly to the pump tube 261, and is configured to deliver fluid in the pump tube 278 in one direction by the driving of the tube pump. Accordingly, blood or dialysate delivered out of the pump tube can be sent into the dialyzer 230 via the blood inlet pipe portion 231 or the dialysate inlet pipe portion 234.

In a region of the panel 220 adjacent to the pump tube 278, hollow flow channels 280 and 490 are disposed in parallel, extending between the upper side and the lower side of the panel 220. The hollow flow channels 280 and 490 have similar configurations.

The hollow flow channel 280, compared with the above-described hollow flow channel 270, is a linear flow channel which does not have diverting flow channels or converging flow channels. An eighth coupling portion 481 and a ninth coupling portion 482 respectively formed on the upper side and lower side of the panel 220 have substantially the same configuration as the first coupling portion 250, including the central constriction. The eighth coupling portion 481 and the ninth coupling portion 482 are coupled by a tube 283 made of resin material. The tube 283 is sandwiched between the sheets 221 and 222, together with the eighth coupling portion 481 and the ninth coupling portion 482. Accordingly, the hollow flow channel 280 is adapted to the large outer diameter of the ends of the eighth coupling portion 481 and the ninth coupling portion 482, and therefore has an inner diameter greater than the inner diameter of the hollow flow channel 270. Into the eighth coupling portion 481, an externally attached tube 2605 is inserted; into the ninth coupling portion 482, an externally attached tube 2606 is inserted.

(Method for Manufacturing Hollow Molded Article 101)

Referring to FIG. 24 to FIG. 33, a method for manufacturing the hollow molded article 101 will be described. The following description is not intended to describe the concrete shape of the hollow molded article 101. Accordingly, the hollow molded article 101 will be described as having a simple shape. A desired hollow molded article 101 may be obtained by preparing a corresponding mold.

Figure 24:
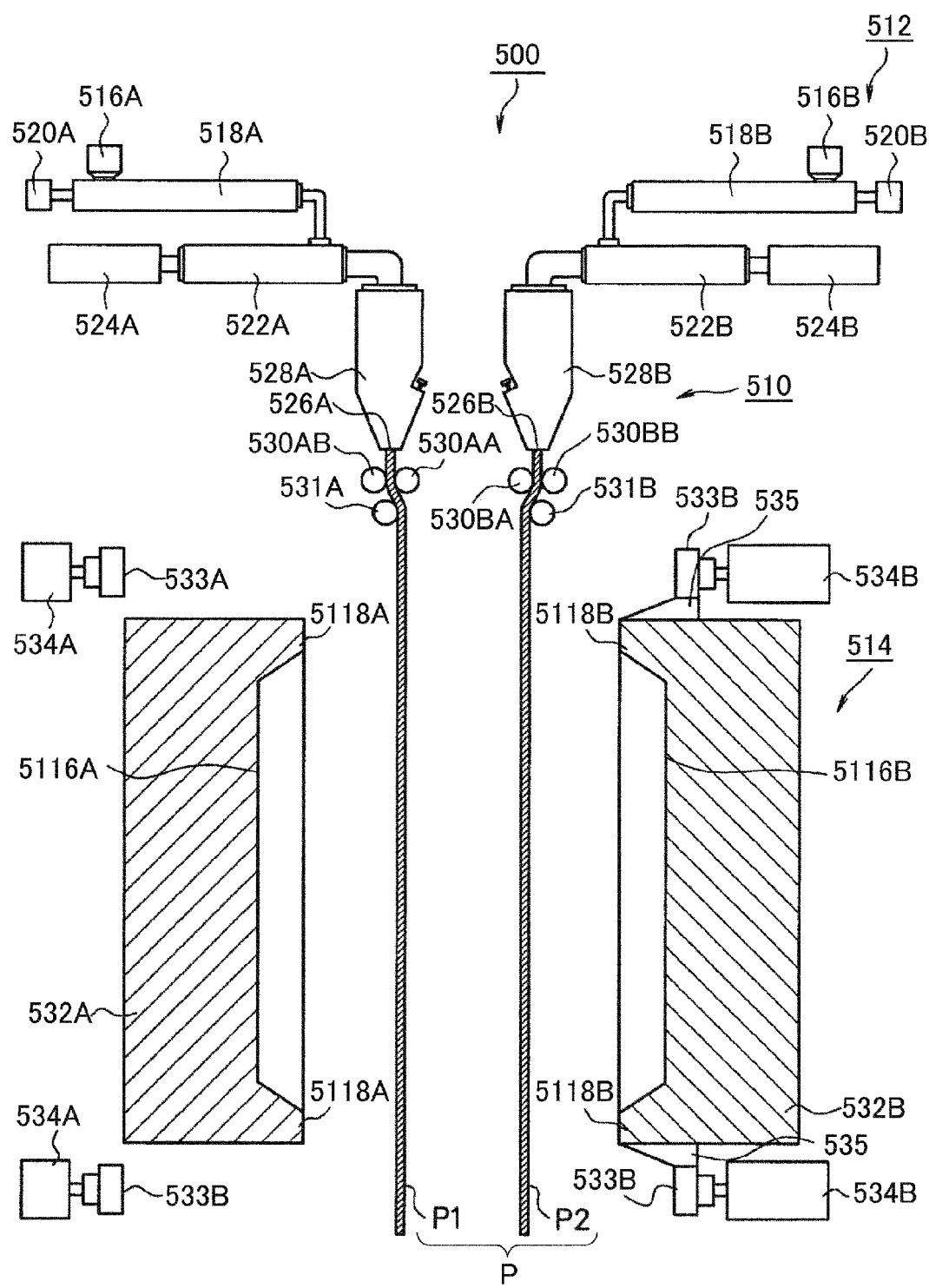
FIG. 24 illustrates a configuration example of a molding device for the hollow molded article.

As illustrated in FIG. 24, a molding device 500 for manufacturing the hollow molded article 101 includes an extrusion device 512, a stretching device 510, and a clamping device 514.

The molding device 500 extrudes a resin sheet P in molten state out of the extrusion device 512 downward. The resin sheet P in molten state being extruded from the extrusion device 512 is stretched by the stretching device 510 and fed to the clamping device 514. The resin sheet P having been fed out of the stretching device 510 is clamped by the clamping device 514. In this way, the hollow molded article 101 having a desired shape is molded.

The extrusion device 512 has the following configuration. The extrusion device 512 includes a cylinder 518 equipped with a hopper 516; a screw (not illustrated) disposed in the cylinder 518; a hydraulic pressure motor 520 coupled to the screw; an accumulator 522; a plunger 524 disposed in the accumulator 522; and a T-die 528. The cylinder 518 communicates with the inside of the accumulator 522. The T-die 528 includes an extrusion slit 526.

First, a predetermined amount of melted and kneaded thermoplastic resin is accumulated in the accumulator 522. The thermoplastic resin accumulated in the accumulator 522 is intermittently extruded from the extrusion slit 526 of the T-die 528 by a predetermined extrusion amount per unit time, the extrusion slit having a predetermined gap. Accordingly, from the extrusion slit 526, the resin sheet P in molten state is extruded at a predetermined extrusion rate.

The stretching device 510 causes a pair of adjust rollers 530A and 530B to move to an open position where the interval between the pair of adjust rollers 530A and 530B, disposed under the extrusion slit 526, is greater than the thickness of the resin sheet P. In this way, the lowest portion of the resin sheet P in molten state being extruded under the extrusion slit 526 can be smoothly supplied to the gap between the pair of adjust rollers 530A and 530B. The timing of increasing the interval of the pair of adjust rollers 530A and 530B to be greater than the thickness of the resin sheet P may be the end of secondary molding on a one-shot by one-shot basis, rather than after the start of extrusion.

Then, the stretching device 510 causes the pair of adjust rollers 530A and 530B to move closer to each other until they reach a closed position. By thus decreasing the interval between the pair of adjust rollers 530A and 530B, the resin sheet P is pinched. Accordingly, the resin sheet P is fed downward as the pair of adjust rollers 530A and 530B is rotated.

Figure 25A:
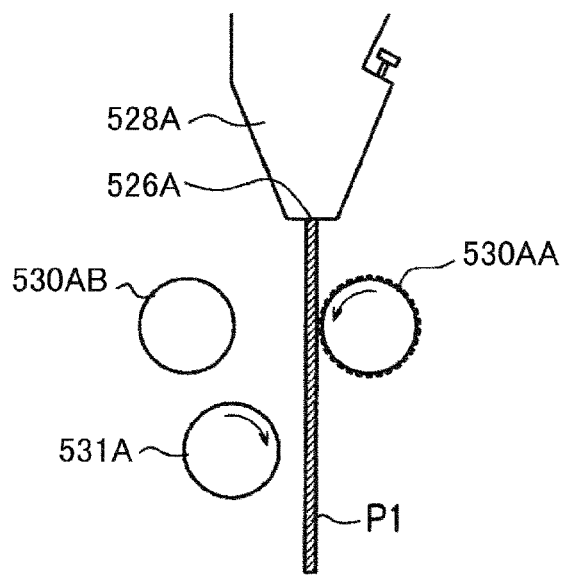
FIG. 25 describes the hollow molded article manufacturing process in greater detail, illustrating the operation of a stretching device.
Figure 25B:
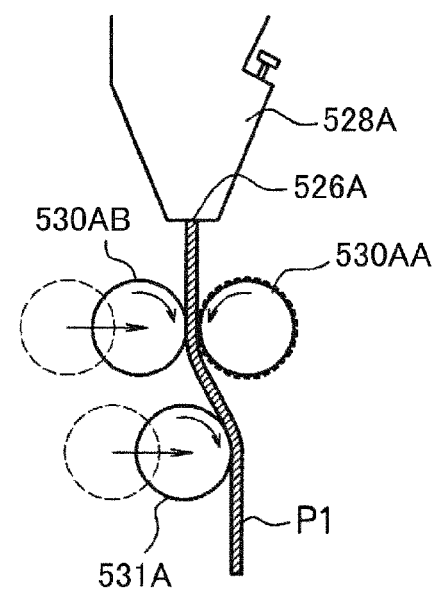

Specifically, after the resin sheet P in molten state is extruded from the extrusion slit 526, as illustrated in FIG. 25(A), a roller moving unit 96 is driven. This causes the pair of adjust rollers 530A and 530B to move closer to each other to the closed position where, as illustrated in FIG. 25(B), the interval between the pair of adjust rollers 530A and 530B is decreased, whereby the resin sheet P is pinched. Accordingly, the resin sheet P is fed downward as the pair of adjust rollers 530A and 530B is rotated. While the resin sheet P in swelled state is fed to the pair of adjust rollers 530A and 530B by the rotation thereof, the rotation speed of the pair of adjust rollers 530A and 530B is adjusted so that the downward feed rate of the resin sheet P by the pair of adjust rollers 530A and 530B becomes greater than or equal to the extrusion rate of the resin sheet P.

More specifically, as the resin sheet P in swelled state is fed out to the pair of adjust rollers 530A and 530B, the length of the resin sheet P hanging downward in the vertical direction increases, causing the thickness of the resin sheet P to be decreased more toward the top of the hanging resin sheet P due to its own weight (draw-down or neck-in). On the other hand, the rotation speed of the pair of adjust rollers 530A and 530B is adjusted so that the feed rate by the pair of adjust rollers 530A and 530B becomes greater than or equal to the extrusion rate. Accordingly, the resin sheet P is pulled downward by the pair of adjust rollers 530A and 530B. In this way, the resin sheet P is stretched and decreased in thickness.

In this case, the rotation speed of the pair of adjust rollers 530A and 530B is decreased over time so that the feed rate becomes closer to the extrusion rate of the resin sheet P.

For example, the rotation speed of the pair of adjust rollers 530A and 530B may be decreased gradually over time while the extrusion rate of the resin sheet P is maintained constant. Alternatively, the extrusion rate of the resin sheet P may be decreased gradually over time while the rotation speed of the pair of adjust rollers 530A and 530B is maintained constant. Further, to the extent that the rotation speed of the pair of adjust rollers 530A and 530B is greater, the rotation speed of the pair of adjust rollers 530A and 530B and the extrusion rate of the resin sheet P may be varied gradually over time.

In any case, the relative speed difference is decreased over time between the downward feed rate of the resin sheet P by the rotation of the pair of adjust rollers 530A and 530B and the extrusion rate of the resin sheet P. Accordingly, at the top of the resin sheet P, the downward pulling force due to the pair of adjust rollers 530A and 530B is decreased, whereby the stretching and thickness reduction due to the pulling force can be relatively decreased, and the thickness reduction associated with draw-down or neck-in is cancelled out. Accordingly, draw-down or neck-in can be effectively prevented, enabling the formation of uniform thickness in the extrusion direction.

In the stretching device 510, as illustrated in FIG. 25(B), when the pair of adjust rollers 530A and 530B are moved closer to each other to the closed position, an auxiliary roller 531 is moved by a roller moving unit toward the adjust roller 530A (drive roller) horizontally, beyond the position of the resin sheet P being pinched between the pair of adjust rollers 530A and 530B. The auxiliary roller 531 is rotated by the roller rotation drive unit in the same rotation direction as the adjust roller (driven roller) 530B. The rotation speed of the auxiliary roller 531 is adjusted so that the feed rate of the resin sheet P by the rotation of the auxiliary roller 531 becomes the same as the feed rate of the resin sheet P by the pair of adjust rollers 530A and 530B. In this way, the auxiliary roller 531 can feed the resin sheet P, which tends to become wound on the driven roller 530B, downward so as to be peeled from the driven roller 530B. As a result, the stretching device 510 can feed the resin sheet P having a uniform and reduced thickness to the clamping device 514.

Figure 26:
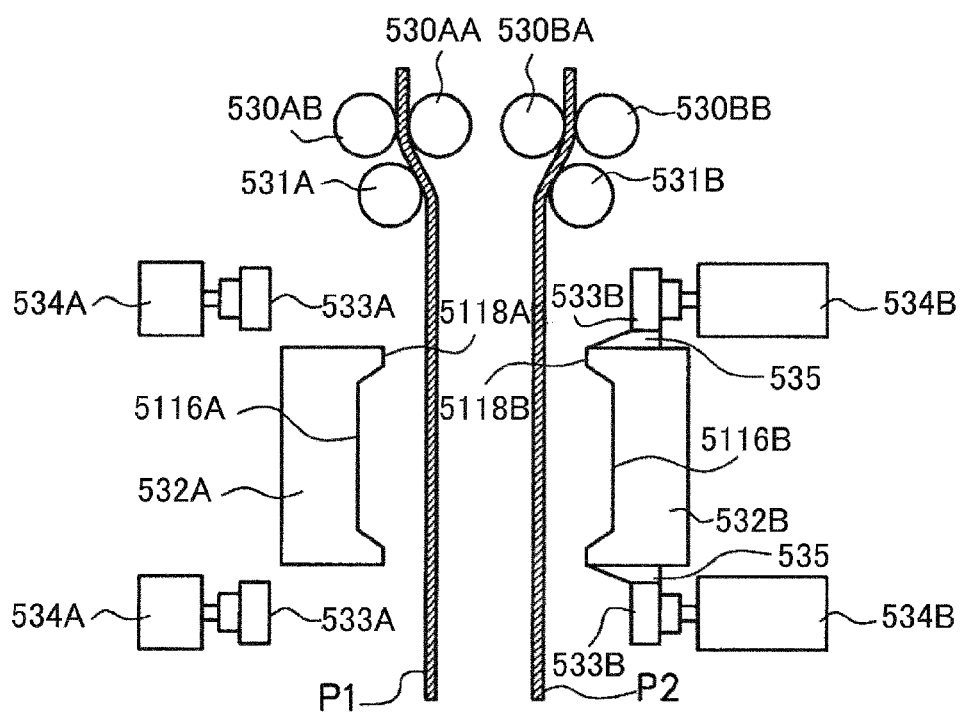
FIG. 26 similarly illustrates a state in which resin sheets are arranged in a clamping device.

Then, as illustrated in FIG. 26, the resin sheet P fed out of the stretching device 510 is disposed between divided molds 532A and 532B. The resin sheet P is positioned so as to extend beyond a pinch-off part 5118. When the positioning of the resin sheet P is complete, the rotation of the pair of adjust rollers 530A and 530B and the auxiliary roller 31 of the stretching device 510 is temporarily stopped with the resin sheet P sandwiched between the pair of adjust rollers 530A and 530B.

The above-described steps are performed for each of the two resin sheets P1 and P2. Then, the resin sheet P1 and the resin sheet P2, which are spaced apart from each other, are disposed between the molds 532A and 532B.

Figure 27:
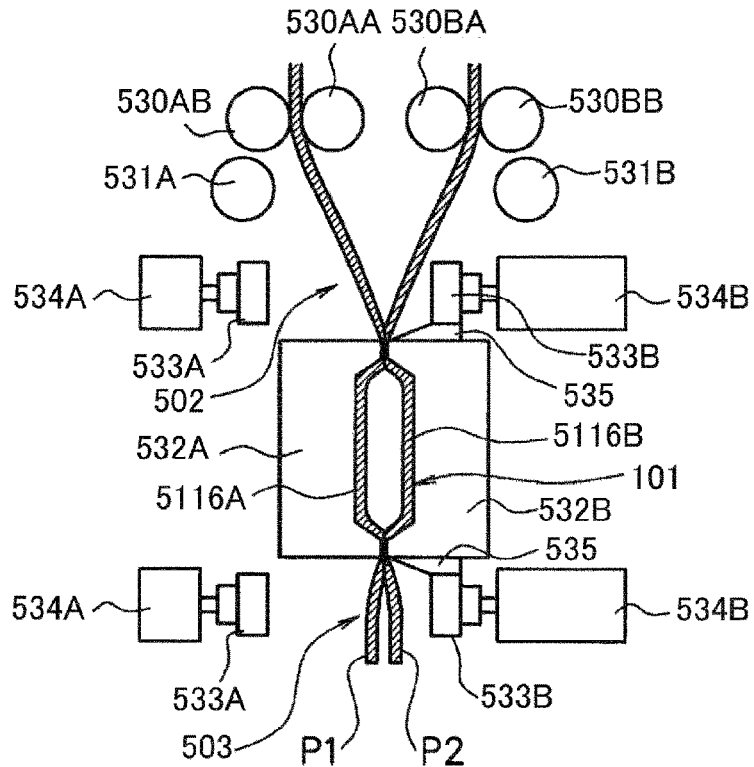
FIG. 27 similarly illustrates a state in which molds of the clamping device are being clamped.

The molds 532A and 532B are then clamped, as illustrated in FIG. 27. The resin sheet P1 is pressed onto a cavity 5116A, whereby the resin sheet P1 is formed in the shape conforming to the irregular surface of the cavity 5116A. The resin sheet P2 is pressed onto a cavity 5116B, whereby the resin sheet P2 is formed in the shape conforming to the irregular surface of the cavity 5116B. Accordingly, the resin sheets P1 and P2 can be molded into the desired hollow molded article 101. When the molds 532A and 532B are clamped, burrs 502 and 503 are produced at the top and bottom of the molds 532A and 532B. The burrs produced at the top of the molds 532A and 532B will be referred to as upper burrs 502. The burr produced at the bottom of the molds 532A and 532B will be referred to as lower burrs 503. In this case, the auxiliary roller 531 is preferably retracted without contacting the resin sheet P. In this way, the upper burrs 2 can be prevented from becoming caught by the auxiliary roller 531.

Figure 28:
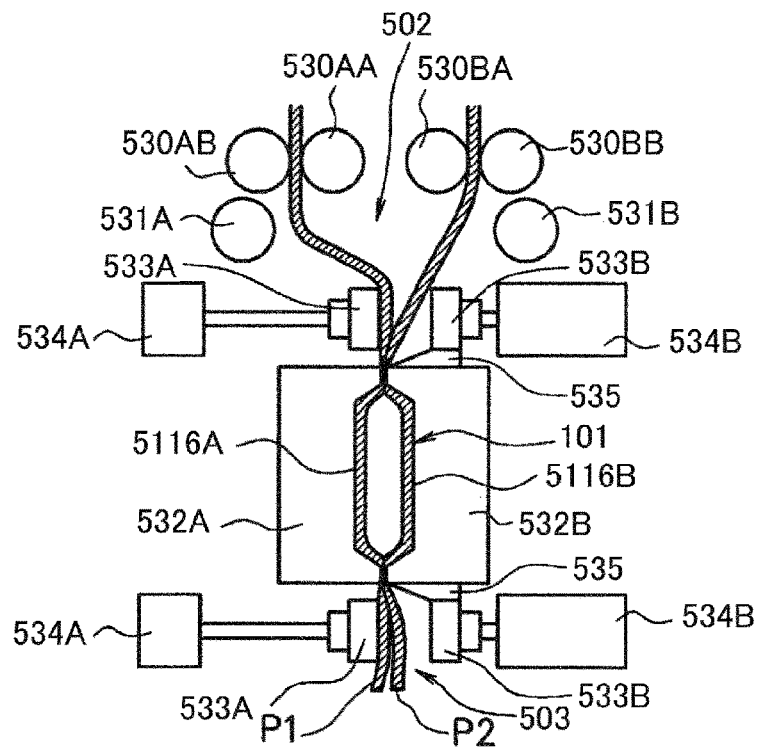
FIG. 28 similarly illustrates a state in which a pressing plate on the pressing side of the clamping device is advanced.

After the clamping of the molds 532A and 532B, a pressing-plate moving device 534A on the pressing side is driven, as illustrated in FIG. 28, so as to advance a pressing plate 533A on the pressing side along the mold 532A. The pressing-plate moving device 534A is configured of an air cylinder, and the pressing plate 533A is advanced by air pressure. After the pressing plate 533A is advanced to a predetermined position, the application of air pressure is stopped.

Figure 29:
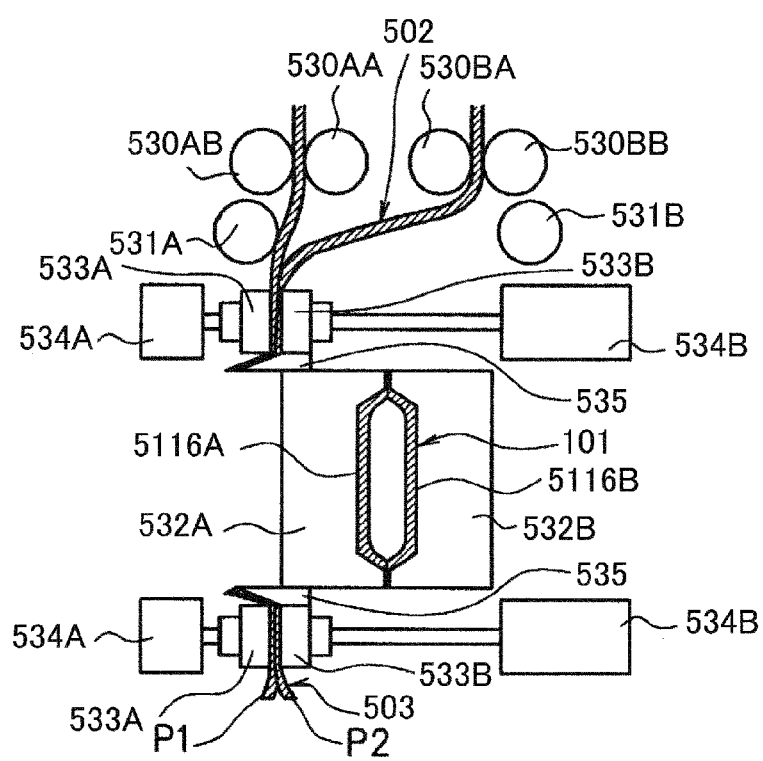
FIG. 29 similarly illustrates a state in which a pressing plate on the cutting side of the clamping device is advanced, thereby cutting burrs.

Thereafter, a pressing-plate moving device 534B on the cutting side is driven, as illustrated in FIG. 29, so as to advance a pressing plate 533B on the cutting side, whereby the burrs 502 and 503 are cut by a cutting blade 535 with which the pressing plate 533B is provided. At this point, the application of air pressure to the pressing-plate moving device 534A on the pressing side is stopped. Accordingly, the pressing plate 533A on the pressing side retracts as the pressing plate 533B on the cutting side advances. The pressing plates 533A and 533B sandwich the burrs 502 and 503, produced at the top and bottom of the molds 532A and 532B, at substantially the same position as the mating face of the molds 532A and 532B. The pressing plates 533A and 533B are moved toward the pressing side with the burrs 502 and 503 sandwiched therebetween, as illustrated in FIG. 28, whereby the burrs 502 and 503 are torn off. Accordingly, even if the cutting blade 535 failed to cut the burrs 502 and 503 completely, the burrs 502 and 503 can be easily torn off where cuts have been formed in the burrs 502 and 503 by the cutting blade 535. As a result, the hollow molded article 101 that has been in a totally burred state with the burrs 502 and 503 attached at the top and bottom can be divided into the three parts of the upper burrs 502, the hollow molded article 101, and the lower burrs 503.

Figure 30:
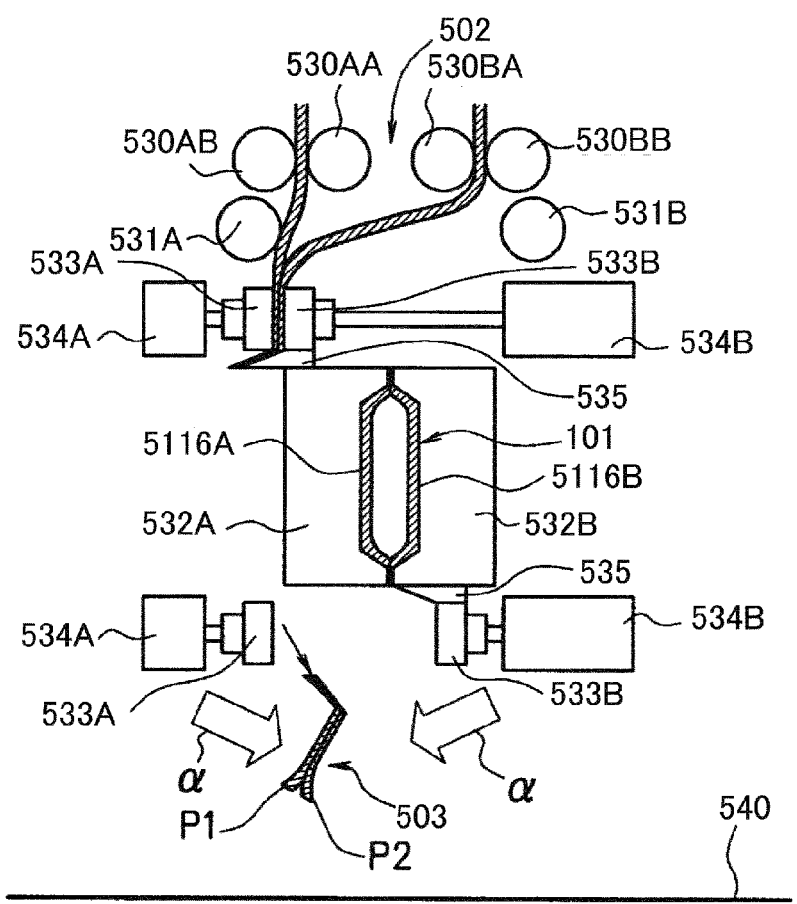
FIG. 30 similarly illustrates a state in which lower burrs have been dropped from the clamping device.

Then, as illustrated in FIG. 30, the pressing plate 533B on the cutting side is retracted, and air $\alpha$ is blown against the lower burrs 503 so as to cause the lower burrs 503 to drop vertically downward. By blowing the air $\alpha$ against the lower burrs 503, the lower burrs 503 can be caused to drop downward without becoming caught by the pressing plates 533A and 533B. The method for blowing the air $\alpha$ is not particularly limited, and the blowing may be performed by any desired method. The lower burrs 503 may be caused to drop at a predetermined position by blowing the air $\alpha$ from both sides of the lower burrs 503 with adjusted air pressures. In this way, the lower burrs 503 can be caused to initially drop on a belt conveyor 540 positioned under the clamping device 514, and then transported.

Figure 31:
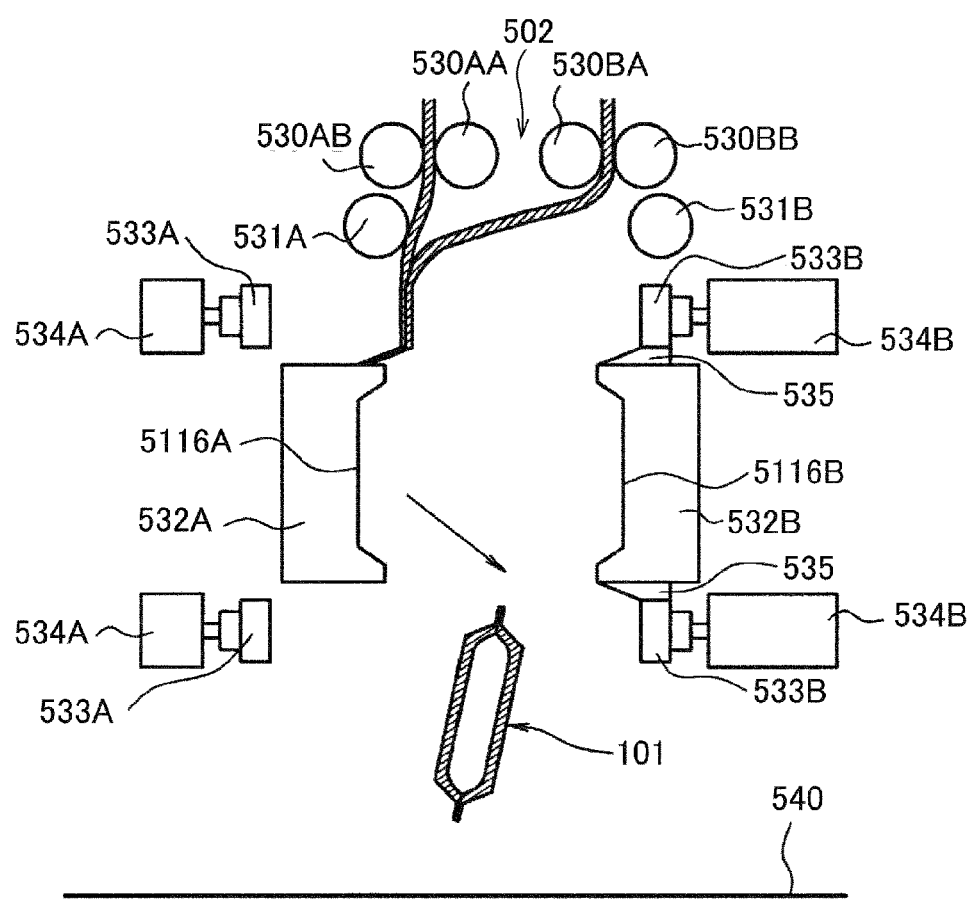
FIG. 31 similarly illustrates a state in which the hollow molded article has been dropped from the clamping device.

As illustrated in FIG. 31, the molds 532A and 532B are then opened, and the desired hollow molded article 101 is caused to drop vertically downward by means of a demolding device (not illustrated). Accordingly, the hollow molded article 101 is dropped on the belt conveyor 540 and transported.

Figure 32:
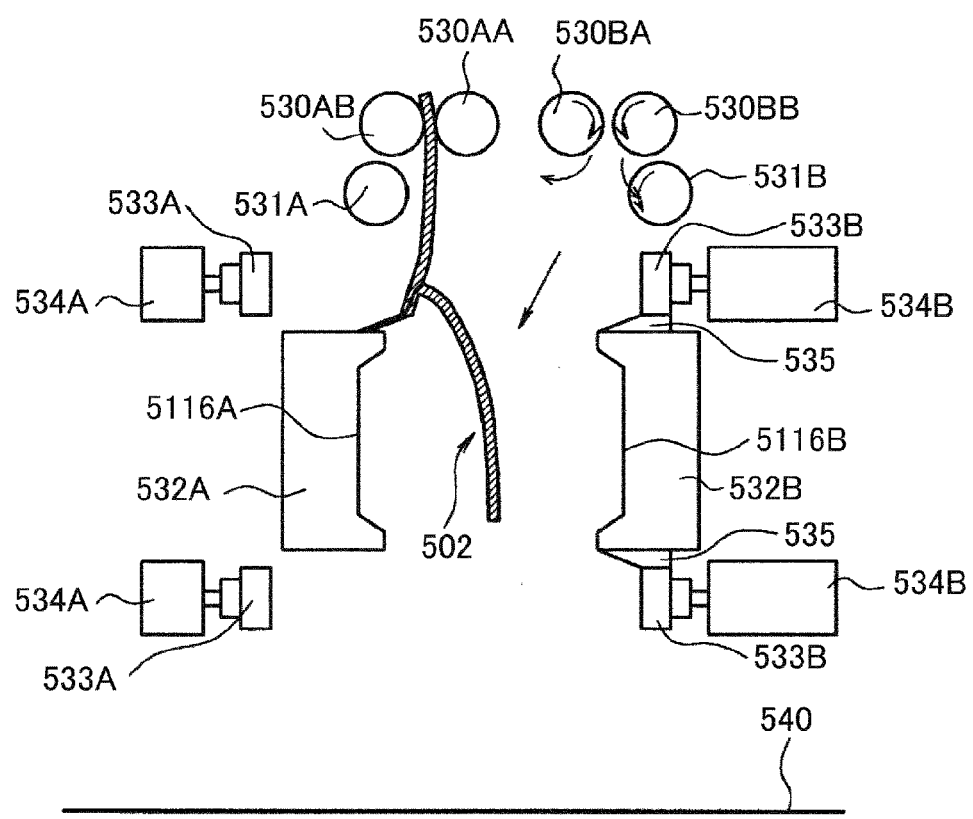
FIG. 32 similarly illustrates a state in which one of upper burrs has been dropped from the stretching device.

Then, as illustrated in FIG. 32, the pair of adjust rollers 530A and 530B and the auxiliary roller 531 on the cutting side are rotated again, so as to release one of the upper burrs 502 being sandwiched between the pair of adjust rollers 530A and 530B.

Figure 33:
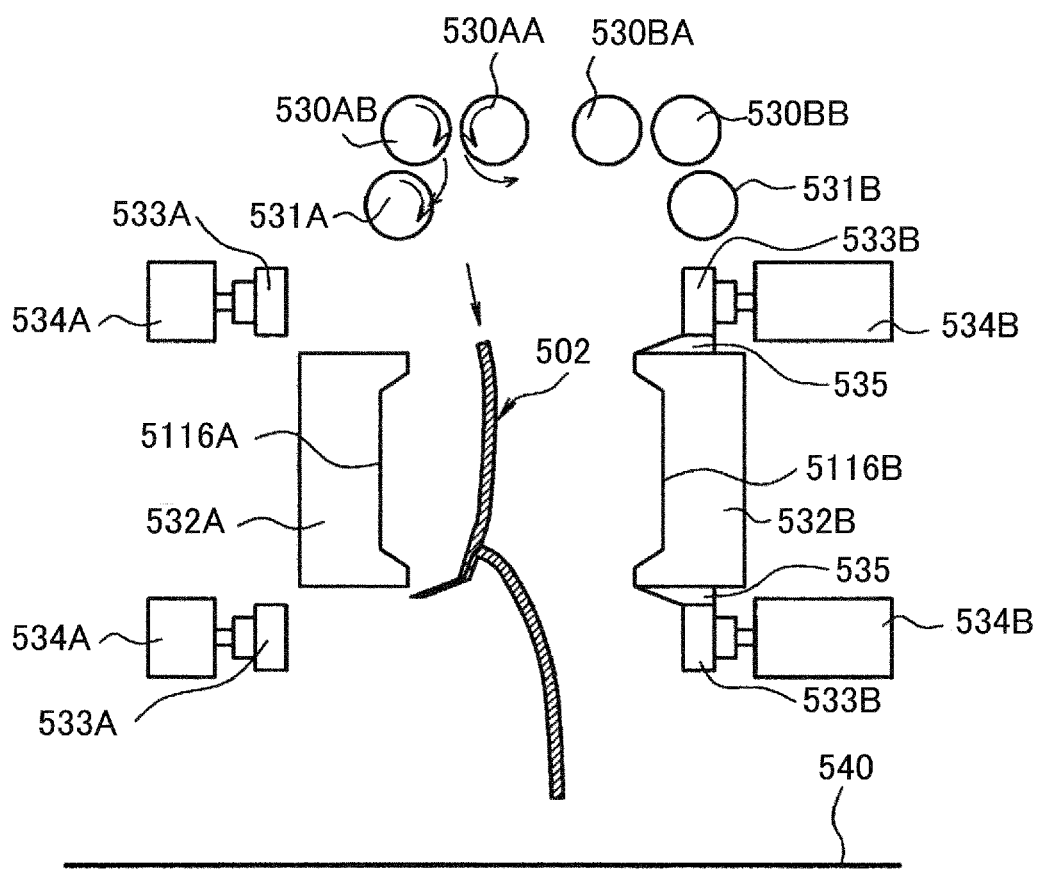
FIG. 33 similarly illustrates a state in which the other of the upper burrs has been dropped from the stretching device.

As illustrated in FIG. 33, the pair of adjust rollers 530A and 530B and the auxiliary roller 531 on the pressing side are again rotated so as to release the other of the upper burrs 502 being sandwiched between the pair of adjust rollers 530A and 530B. Accordingly, the upper burrs 502 are dropped on the belt conveyor 540 and transported.

In the clamping device 514, the three divided parts, i.e., the upper burrs 502, the hollow molded article 101, and the lower burrs 503, are dropped on the belt conveyor 540 in the order of the lower burrs 503, the hollow molded article 101, and the upper burrs 502, with time lags, and then transported. Because the lower burrs 503, the hollow molded article 101, and the upper burrs 502 are transported in that order by the belt conveyor 540, the hollow molded article 101 alone can be easily picked out of the belt conveyor 540, using detection sensors and the like. The lower burrs 503 and upper burrs 502 can be reutilized as recycled material.

While the present invention has been described with reference to the examples, the technical scope of the present invention is of course not limited to the scope of description of the examples. Persons skilled in the art will recognize that various modifications and improvements can be made to the examples. That examples incorporating such modifications or improvements are also included in the technical scope of the present invention will be obvious from the claims.

The invention claimed is:

1. A hollow molded article comprising:
   a panel including a first resin sheet and a second resin sheet welded together by a reduced-thickness welded portion provided on both sides of a flow channel along a side edge of the flow channel;
   a parting line formed at a boundary of the first resin sheet and the second resin sheet, the parting line being a seam where the first resin sheet and the second resin sheet meet, wherein a plurality of apertures are formed within the parting line; and
   the flow channel disposed between the first resin sheet and the second resin sheet, and including a connection portion for external connection disposed on a peripheral edge of the panel, wherein
   the connection portion is formed by the first resin sheet and the second resin sheet,
   the connection portion is a protruding pipe,
   the protruding pipe comprises first and second protruding pipes that communicate with the flow channel and protrude externally from the peripheral edge of the panel, each of the first and second protruding pipes including an opening portion at a tip end thereof,
   the reduced-thickness welded portion has a thickness that is smaller than a total thickness of the first resin sheet and the second resin sheet, and extends from a first root of the first protruding pipe to a second root of the second protruding pipe,
   at least one of the first and second protruding pipes includes a cylinder portion with a stepped protrusion disposed on an outer surface at substantially a tip end of the cylinder portion, the stepped protrusion having steps becoming higher with increasing distance from the tip end of the cylinder portion,
   the hollow molded article further comprises a hinge portion, wherein the hinge portion consists of two hinge portions proximate and substantially parallel to each other, and the panel is divided into a first section and a second section having the two hinge portions disposed therebetween, and a third section disposed between the two hinge portions, the flow channel is provided in the first section and/or the second section, and a thickness of the third section is larger than thicknesses of the hinge portions,
   the flow channel comprises a functional component accommodating portion which accommodates a functional component which is a filter or a static mixer,
   the functional component accommodating portion is provided in the first section, and the second section is provided with an opening portion at a location opposing the functional component accommodating portion when the hollow molded article is folded at the two hinge portions,
   the hollow molded article further comprises a dialyzer including two dialysate circulation pipe portions protruding from a side surface thereof and the dialyzer is fixed to the panel,
   the panel includes first and second attachment sections each including a cut-out,
   the first attachment section extends vertically upward at substantially a center of an upper side of the panel,
   the second attachment section extends vertically downward at substantially a center of a lower side of the panel,
   each of the cut-outs of the first and second attachment sections includes, on an opening side thereof, two narrowing portions decreasing a width of the cut-out and having a convex shape, and on a side opposite to the opening side, an inner peripheral portion having a semi-circular arch shape,
   the cut-outs of the first and second attachment sections open to the same direction, and the hollow molded article is configured such that the dialyzer is fixed to the panel with each of the circulation pipe portions fitted in each of the cut-outs beyond the narrowing portion of each cut-out of the first and second attachment sections,
   the circulation pipe portions of the dialyzer each include, around the pipe, a flange portion having an annular groove provided over an entire circumference thereof along a circumferential direction, and the hollow molded article is configured such that the dialyzer is fixed to the panel with each of the semi-circular inner peripheral portions of the cut-outs of the first and second attachment sections fitted in each of the annular grooves of the flange portions,
   the panel includes reduced-width portions and a central cut-out formed by cutting out a central region of a lateral side of the panel, the central cut-out being sandwiched by the reduced-width portions,
   each of the reduced-width portions includes a coupling portion which is sandwiched by the first and second resin sheets,
   the coupling portions each include a first side facing the central cut-out and a second side facing outside,
   the coupling portions of the reduced-width portions are connected by inserting one end and the other end of a pump tube located in the central cut-out into the first side of each of the coupling portions,
   externally attached tubes are inserted into the second side of each of the coupling portions,
   each coupling portion has a shape which includes a constriction at substantially the center in an axial direction thereof, and
   a diameter of the first side is larger than a diameter of the second side.

2. The hollow molded article according to claim 1, wherein
   the flow channel includes an agitation promoting portion, and
   the agitation promoting portion includes one or more of a large diameter portion and one or more of a small diameter portion alternately disposed along a longitudinal direction, the one or more small diameter portion having a diameter smaller than a diameter of the one or more large diameter portion.

* * * * *